US009364597B2

(12) United States Patent
Wolff et al.

(10) Patent No.: US 9,364,597 B2
(45) Date of Patent: Jun. 14, 2016

(54) BLOOD ULTRAFILTRATION SUBSTITUTION TARGET METHOD AND DEVICE

(75) Inventors: Henrik Wolff, Witzenhausen (DE); Stefan Moll, Hamburg (DE)

(73) Assignee: B. BRAUN AVITUM AG, Melsungen (DE)

( * ) Notice: Subject to any disclaimer, the term of this patent is extended or adjusted under 35 U.S.C. 154(b) by 356 days.

(21) Appl. No.: 13/885,603

(22) PCT Filed: Nov. 15, 2011

(86) PCT No.: PCT/DE2011/001989
§ 371 (c)(1),
(2), (4) Date: Jul. 29, 2013

(87) PCT Pub. No.: WO2012/095066
PCT Pub. Date: Jul. 19, 2012

(65) Prior Publication Data
US 2013/0303961 A1  Nov. 14, 2013

(30) Foreign Application Priority Data

Nov. 17, 2010  (DE) .................. 10 2010 052 070

(51) Int. Cl.
*A61M 1/14* (2006.01)
*A61M 1/16* (2006.01)
*A61M 1/34* (2006.01)

(52) U.S. Cl.
CPC . *A61M 1/14* (2013.01); *A61M 1/16* (2013.01); *A61M 1/342* (2013.01); *A61M 2205/3331* (2013.01); *A61M 2205/52* (2013.01)

(58) Field of Classification Search
CPC ......... A61M 1/14; A61M 1/16; A61M 1/342; A61M 2205/3331; A61M 2205/52; A61M 1/3441
See application file for complete search history.

(56) References Cited

U.S. PATENT DOCUMENTS 5,431,811 A      7/1995  Tusini et al.
7,131,956 B1 *  11/2006  Pirazzoli et al. ............. 604/6.09
(Continued)

FOREIGN PATENT DOCUMENTS

DE      102 01 109      1/2003
DE      103 55 042      6/2005
(Continued)

OTHER PUBLICATIONS

International Search Report for PCT/DE2011/001989 mailed Apr. 25, 2012.

*Primary Examiner* — Tatyana Zalukaeva
*Assistant Examiner* — Benjamin Klein
(74) *Attorney, Agent, or Firm* — RatnerPrestia

(57) ABSTRACT

The present invention relates to a method as well as a blood treatment unit for the implementation of this method for the best possible attainment of a predetermined substitution target during the ultrafiltration of blood. According to the invention, a method and a blood treatment unit for the implementation of the method is provided, wherein it is determined by detection of pressure measurement values in the blood treatment unit whether the calculated substitution target is achieved at the end of the dialysis session or not and in case of the result that the calculated substitution target cannot be achieved with the current dialysis parameters, an adjustment of the flow rate of blood, dialysate and/or substituate is performed in order to achieve the substitution target for a given treatment time in an optimal way or modify the treatment time for the given substitution target as little as possible.

18 Claims, 6 Drawing Sheets

(56) References Cited

U.S. PATENT DOCUMENTS

| | | |
|---|---|---|
| 2003/0136181 A1 | 7/2003 | Balschat et al. |
| 2005/0203493 A1 | 9/2005 | Kuroda et al. |
| 2006/0157408 A1 | 7/2006 | Kuroda et al. |
| 2007/0108128 A1 | 5/2007 | Kopperschmidt et al. |
| 2008/0215247 A1 | 9/2008 | Tonelli et al. |
| 2010/0168925 A1 | 7/2010 | Hilgers et al. |
| 2011/0240555 A1 * | 10/2011 | Ficheux et al. ............... 210/637 |

FOREIGN PATENT DOCUMENTS

| | | |
|---|---|---|
| EP | 0 240 101 | 10/1987 |
| EP | 1 175 917 | 1/2002 |
| WO | WO 2007/140993 | 12/2007 |
| WO | WO 2010040927 A1 * | 4/2010 |

* cited by examiner

BLOOD ULTRAFILTRATION SUBSTITUTION TARGET METHOD AND DEVICE

CROSS REFERENCE TO RELATED APPLICATIONS

This application is the U.S. national phase application of PCT International Application No. PCT/DE2011/001989 filed Nov. 15, 2011, which claims priority to German Patent Application No. DE 10 2010 052 070.5 filed Nov. 17, 2010, the contents of each application being incorporated by reference herein.

FIELD OF THE INVENTION

The present invention relates to a method as well as a blood treatment unit for the implementation of this method for the best possible attainment of a predetermined substitution target in the ultrafiltration of blood. According to aspects of the invention, a method and a blood treatment unit for the implementation of the method is provided, wherein it is determined by the measurement of pressure measurement values in the blood treatment unit whether the calculated substitution target is achieved at the end of the dialysis session or not and in case of the result that the calculated substitution target cannot be achieved with the current dialysis parameters, an adjustment of the flow rate of blood, dialysate and/or substituate is performed in order to achieve the substitution target for a given treatment time in an optimal way or modify the treatment time for the given substitution target as little as possible.

The invention relates thereby to the field of the filtration, more precisely said the tangential flow filtration TFF. Here, the fluid to be purified is separated by a semipermeable membrane from the purification solution. The purification solution is also described as dialysis solution or dialysate. The dialysate has, according to the requirements, different properties due to the dissolved substances which are used for the dialysis. The concentration of the compounds in the dialysate depends on the kind of the compounds in the fluid, the dialysis time, the age and body weight of the patients, the symptoms to be controlled and other conditions. Dialysis solutions are produced in general before use from dialysis concentrate and water. Typically the purification solution has a lower concentration of the substances which should be removed from the fluid to be purified, than the fluid to be purified itself. By this concentration gradient diffusion across an exchange surface is generated. To use optimally the diffusion as purification force, tangential flow filter are typically operated using the countercurrent principle.

BACKGROUND INFORMATION

A dialysis filter consists substantially of hollow fibers, i.e. cylindrical fibers, which traverse a housing longitudinally stretched. Thereby, the walls of the hollow fibers work due to semipermeable structures as membranes. At their ends, the hollow fibers are embedded in a casting compound. In the dialysis filter, the hollow fibers can be combined into modules with several square meter filter surface. In the dialysis by tangential flow filtration, also known as cross-flow filtration, blood/plasma is supplied to the hollow fibers by a first fluid circulation, which flows through them lengthwise. By a second fluid circulation, the dialysate is supplied usually by the countercurrent principle, but if possible also parallel to the blood stream. The housing thus has four ports, namely for each fluid stream two, one for supply and removal, respectively. On the inside of the hollow fiber membrane is thus the blood stream, and on the outside is the dialysate.

Another purification mechanism is convection. Here a pressure gradient across the semipermeable membrane is generated, whereby the fluid to be purified is pressed over the semipermeable membrane. Thereby, the substances are washed away in its current concentration. This purification process is not dependent on the concentration of substances in the purification solution, decisive are hereby only the concentration in the fluid to be purified, and the membrane properties, such as sieving coefficient, permeability etc. It is therefore of interest to know the filter properties at the beginning of the treatment as well as during the treatment.

A specific area of the filtration is the extracorporeal blood treatment for chronic or acute renal failure. Here, the fluid to be purified is the blood of the patient and the purification solution is the dialysate. In this specific case of the TFF it is decisive to replace in the treatments (in the chronic case typically three times per week) the blood purification function of the kidney as effective as possible. To ensure this, the Kt/V value has been established as measure of the treatment quality. The Kt/V is a parameter to determine the dialysis effectiveness and a key element for the evaluation of the dialysis efficiency. K is the clearance, which is determined by the urea content of the blood before and after the dialysis. The value t shows the effective dialysis time in minutes and V is the urea distribution volume. This refers to the content of water in the body which represents around 60% of the body mass. The aim of a treatment is to achieve a $Kt/V \geq 1.2$. In a normal treatment process values are achieved, which meet this criterion in general. However, adversities can occur during treatment, which affect negatively the treatment process as well as the treatment result. It is therefore important to monitor and control the influencing parameters during a treatment in order to be able to react to such adversities in a fast and especially targeted manner and to adjust the system parameters during the dialysis accordingly.

In modern dialyzers purification is achieved by use of convection due to the principle of the ultrafiltration. Hereby, not only substances to be removed or uremic substances are removed from the blood. Due to the applied pressure gradient (transmembrane pressure) across the filter membrane by the ultrafiltration pump (UF pump), plasma is convectively removed from the blood via the membrane. For this purpose, on the dialysate side from a closed system, a defined amount of dialysis solution is removed. Thereby, in the closed system, a negative pressure is generated which ensures that the same amount of blood passes over the semipermeable membrane to the dialysate side.

The loss of plasma volume must be compensated by supplying substituate solution. The substituate solution is typically an electrolytic solution. The ultrafiltration rate (UF-rate) describes the volume of the blood plasma deprive in such a manner per time unit and thus also the volume of substituate solution which must be fed back into the blood. The admixture of the substituate is performed either before the dialyzer (predilution) or after the dialyzer (postdilution). The upper limit for the substituate solution is typically 25-30% of the blood flow in the postdilution for a hemodiafiltration (HDF). For the predilution mode this limitation does not exist.

The substitution thus continuously compensates the fluid removed via the liquid deprivation by the ultrafiltration and avoids thereby volume losses. Thereby the substitution rate is defined by a specific volume per time unit.

The spent dialysis solution is replaced respectively by an equal volume of fresh dialysis solution. This can be done in a so-called balance chamber. Modern systems achieve here a maximum deviation of 0.07% during a several-hour dialysis session. To prevent mixing of the spent dialysis solution with the fresh dialysis solution, the two chambers are separated by a rubber membrane from each other.

A decisive process is the interaction of the filter membrane with blood. By this interaction the flow properties of the filter deteriorate both in transmembrane direction and in blood flow direction. These changes are caused for example by thrombocyte attachment on the membrane, clotting, chemical binding of blood components to the membrane or simply mechanical (flow-induced) pressing of the blood components on and even into the membrane.

Transmembrane direction or transmembranous herein refers to a flow of the blood over the membrane of the dialyzer or dialysis filter.

During clotting a gelatinous aggregation of red blood cells (erythrocytes) stabilized by fibrin filaments is formed. Unlike the term thrombus a coagulum describes a blood clot, which is located outside of a blood or lymph vessel (extravascular) and not inside (intravascular).

These and other changes of the system properties have various effects on the treatment process and the treatment quality. Especially, the treatment by hemodiafiltration is affected thereby, because here it is focused on the convective substance transport of medium molecular substances. The flow and stream properties changed especially by the deposits on the filter membrane lead to a changed demand for dialysis solution. By deterioration of the transmembrane flow properties or the permeability, also the sieving coefficient for uremic substances in the medium molecular weight range deteriorates, which has the result that by the same amount of convectively filtered fluid less uremic substances are removed from the blood circulation. Another effect is the reduction of the effective flow area, both in blood flow direction and in transmembrane direction. This results in a reduction of the active filter surface whereby it can lead to a deterioration of the diffusive purification. With new filters there is usually a buffering potential that is larger than the maximum physiologically filtering. Thereby, a reduction of the effective flow area can be limited to a certain degree. However, if this potential is exhausted, it leads to the above-described effect.

As suitable counteractions, or reactions to such changes, rinsing with saline for "cleaning" of the dialyzer, the addition of heparin to prevent further clotting or lowering of the ultrafiltration rate (UF) in order to reduce the hemoconcentration are generally accepted. The permeability of the membranes is determined by measuring the fluid volume, which passes at a given pressure difference at a temperature of 37° C. through a predetermined membrane surface the membrane and which is normalized for general comparability in terms of area unit, time unit, and pressure unit. As fluid for determining the ultrafiltration rate water is used.

DESCRIPTION OF THE RELATED ART

From the prior art, experiments are already known which have the aim to recognize system changes and react to them. In the US 2008/0215247 A1 it is assumed that the linear relation between transmembrane pressure (TMP) and ultrafiltration rate $Q_{UF}=TMP*K_{UF}$ ($K_{UF}$=ultrafiltration coefficient) meets only in a certain range of the TMP. Thus, firstly the function $Q_{UF}$ (TMP) is estimated by increasing the TMP gradually and measuring the thereby generated ultrafiltration rate. From a certain value an increase of TMP results in an ever less increase of the ultrafiltration rate. Therefore the knee point (tangent point) of the function $Q_{UF}$(TMP) is selected as working point. Since $K_{UF}$ deteriorates during the treatment due to the system change, tWO 2006/011009 A2 discloses the technical conditions to determine the relation between TMP and $Q_{UF}$ on hourly basis.

In the EP 1175917 A1 as a further concept, the adjustment of the ratios from pre- and postdilution in the process of the treatment is described. Both terms pre- and post-dilution refer to at which point—before or after the pass of the blood through the dialysis filter—a volume substitution of the blood preferably with an electrolyte solution and thus a dilution of the blood is carried out.

Since the substituate solution is fed directly into the blood of the patient, it is in the nature of things, to use for the substituate solution sterile, pyrogen free components or concentrates of infusion-suitable quality produced under GMP (good manufacturing practice) conditions. Hereby procedures like in-line attenuation of all parts of the production facilities, bacterial filtration of the product, in-process controls (filter density, concentration control), quantitative final control and documentation of manufacturing and quality control are used. The composition of the substituate solution corresponds approximately to that of the dialysate. The elaborate production of substituate solutions causes high production costs, which are reflected in the financial costs of dialysis treatments.

Different dialyzers or filters require based on various properties different dialysis processes and consume different amounts of dialysate and substituate fluid. The information about the used dialyzers and particularly about the filters installed in the used dialyzers is often not known to the operating staff so that the dialysis process and especially the required volumes of dialysate, but particularly of substituate fluid, cannot be precisely determined.

The need for dialysate and substituate fluid varies further depending on the dialysis progress so that a desired substitution target can often not be achieved. There is therefore a need for a device and a method which can on the one hand determine the filter properties and incorporate the calculation of a substitution target adapted to the individual patient, because the substitution target is substantially determined by the filter properties. On the other hand the device and the method should be able to achieve at the end the calculated substitution target in an optimal way by adjusting parameters of the dialysis session.

As used herein, the term "dialyzer" which is synonym to "transmembrane filter" describes the housing with inlet and outlet for the dialysate as well as inlet and outlet for the blood, wherein the filter is in the housing. As filter, preferred hallow fibers are used, which are flowed inside by the dialysate, and outside along the hollow fibers, the blood flows, and the substances to be removed pass through the porous hollow fibers by diffusion and convection from the blood into the dialysate. The term "filter properties" refers to the properties of the dialyzer or transmembrane filter with respect to the blood purification. As filter properties, especially the surface of the filter, the pore density and pore size as well as the pore size distribution are crucial.

SUMMARY OF THE INVENTION

According to aspects of the invention this object is solved by the methods and the devices which are mentioned in the independent claims. Further advantageous embodiments of the invention are the result of the dependent claims, the description, the figures as well as the examples.

The present invention relates to a method for calculating or determining a substitution target in the form of the required volume of substitution fluid in blood treatment units by t determination of pressure measurement values as well as to a blood treatment unit which is suitable for this method. The invention relates particularly to a device, i.e. a blood treatment unit, which is adapted in such a manner to achieve a predetermined and defined substitution target by monitoring of the dialysis process and if necessary, adjustment of the dialysis parameters and thereby changing an estimated dialysis session duration as little as possible, in particular extending it as little as possible, or to achieve the substitution target in an optimal way during a determined dialysis session period of for example, 4 hours, 4.5 hours or 5 hours. According to aspects of the invention, the blood treatment unit is not only adapted to achieve a calculated substitution target in the given time at the best or to achieve a determined substitution target and to change the estimated treatment time as little as possible, but also to calculate a substitution target preferred in regard to the actual patient and adjusted to the currently used dialyzer or filters. Since the dialyzers are disposable and thus consume materials, it is common that a patient at various dialysis sessions also receives various filters or dialyzers. Since the substitution target depends critically on the respective filter, the blood treatment unit is adapted so that before the actual dialysis session the properties of the currently used filter are determined by a reference solution. If the specifications of the filter which is above all the effective filter surface as well as the permeability, are stored on storage unit of the blood treatment unit, by means of the reference solution also the precise type of filter and not only the filter properties can be determined. Based on the determined filter properties or even the specific filter type, a suitable substitution target is calculated. Thereby suitable does not mean a maximum substitution target of for example, 30 L per dialysis session, i.e. per dialysis treatment. Since a suitable substitution target should be adjusted to the individual patient, too, preferably the patient data from previous dialysis sessions such as dialysis substitution targets achieved in previous sessions or also data of a patient group similar to or comparable with the individual patient are taken into account. Thus, usually suitable substitution targets result in the range of 15 L to 28 L, more preferably 17 L to 27 L, more preferably 19 L to 26 L, and even more preferably 21 L to 25 L per dialysis session. During the next dialysis session either the substitution target is determined as goal that is to be achieved and thereby from an estimated treatment time deviated as little as possible or the treatment time is determined and from the calculated suitable substitution target it shall be deviated as little as possible. Whether the treatment time can be met at a determined substitution target or the substitution target is achieved during a determined treatment time, is determined by recording of pressure measurement values by at least two pressure sensors during the blood treatment, which are compared with reference pressure measurement values, which should be available if the substitution target will be achieved at the end of the blood treatment. If this comparison shows matching of the detected pressure measurement values within a tolerance range with the reference pressure measurement values, then the substitution target will probably be achieved at the end of the blood treatment and the dialysis parameters are all right. However, if the comparison of the detected pressure measurement values with the reference pressure measurement values within a tolerance range shows a deviation beyond the tolerance range, then the substitution target will not be achieved at the end of the dialysis session and the dialysis parameters must be readjusted. As dialysis parameters suitable for the readjustment, the blood flow rate, the flow rate of the dialysate (i.e. the dialysis fluid), and the flow rate of the substituate are used. Thus, it is ensured that for the actual patient an optimal dialysis session is performed, which is not necessarily to be equated with optimal blood purification, but with a most tolerable dialysis treatment for the actual patient with the use of a specific filter or dialyzer. No blood treatment unit of the prior art enables the determination of the filter properties or the specific filter type before the blood treatment for calculating a substitution target most tolerable for the patient for the current dialysis session, taking into account the filter properties and provides embodiments which readjust the dialysis parameters in order to achieve this most tolerable substitution target at the end of the blood treatment.

DETAILED DESCRIPTION OF THE INVENTION

The present invention relates to a blood treatment unit with a dialyzer, at least two pressure sensors, a central processing unit, and a storage unit adapted to perform the following method:
a) Determining the filter properties by detecting at least two pressure measurement values at the at least two pressure sensors within the blood treatment unit using a reference solution,
b) Optionally comparing the detected pressure measurement values with reference values of the same patient saved on the storage unit which were detected during previous dialysis sessions or with reference values of a patient group saved on the storage unit,
c) Calculating a substitution target based on the values according to step a) and optionally step b),
d) Measuring of pressure measurement values at the at least two pressure sensors during a blood treatment,
e) Comparing the pressure measurement values measured according to step d) with reference pressure measurement values saved on the storage unit, and
f) Adjusting the blood flow rate, dialysate and/or substituate in case of deviation of at least one detected pressure measurement value from the reference pressure measurement value, in order to achieve the substitution target for a given treatment time in an optimal way or to modify the treatment time for a given substitution target as little as possible.

The invention is advantageous because it covers the determination of the filter properties at the beginning of the dialysis, and allows predetermination of the probable dialysis process. Thereby, even before the beginning of the actual treatment the best possible process of dialysis and the demand for substitution fluid can be determined.

Reference pressure measurement values are preferably those which have been recorded during a blood treatment, in which the substitution target has been achieved.

The invention refers in particular to a device for carrying out a method and to a method, in which, from pressure measurement values at a blood treatment unit, an optimal substitution target is determined at the start of dialysis and in the course of disturbances occurring during the dialysis session where appropriate certain parameters can be adjusted. The optimal substitution target is defined by the necessary, predetermined volume of substituate which is or should be supplied again to the bloodstream. The substituted volume can thereby be calculated by the substitution rate over the time of liquid exchange. It is essential to the invention that the substitution rate is dynamically adapted to varying conditions, as they may change the optimum during the dialysis session.

The substitution rate is thereby defined by a determined volume per time unit. The substitution rate can be expressed for example, by ml/min or l/h. As supplied volume of the substituate are supplied 1-10 L per treatment hour, preferred 1-9, more preferred 2-8, even more preferred 2-7.5, even more preferred 2.5-7, even more preferred 2.5-6.5, even more preferred 2.5-6, even more preferred 3-5.5 and most preferred 4-5 L/h.

The dialysis session lasts overall between 4 and 5 hours, so that the substitution target is generally between 20 L to 26 L per dialysis session.

The substitution target can be determined preferably from the blood flow rate, i.e. the streaming blood volume per time unit according to:

$$Q_{sub}=[(\tfrac{1}{3}+BF*T)-WL]*p, \quad (1)$$

wherein BF is the blood flow rate, T is the treatment time and p is a flow-specific factor that is determined by the pressure measurements using a reference solution and reflects the mathematic relation between pressure measurement values and flow rate. The factor p can be determined from a matrix, in which permeability and filter surface are plotted against each other (FIG. 3).

The substitution target can be determined preferably also using a maximal hematocrit according to:

$$Q_{sub}=[BF*\{1-[Hct(\text{one})/Hct(\max)]\}-WL]*p, \quad (2)$$

wherein WL is the weight loss that causes by the amount of fluid which has been deprived effectively from the patient during the treatment and is not substituted. The hematocrit is detected at sensors which can be or are present at the dialysis device, if the hematocrit should be used for the calculation of the substitution target.

The substitution target can be determined preferably also using a predetermined, non-membrane-permeable blood component or a group of components X, hence, large proteins, blood cells and the like according to:

$$Q_{sub}=[BF*\{1-[X(\text{one})/X(\max)]\}-WL]*p, \quad (3)$$

It is important to consider that not exactly the same amount of fluid removed from the blood is fed back as substituate to the blood, but that in the dialysis procedure also excess fluid is removed from the patient, which he cannot eliminate, and which is described as so-called "weight loss". The substituate and the "weight loss" are the so-called convective volume.

According to aspects of the invention the term flow rate relates to the flowing fluids, i.e. blood, dialysate as well as substituate fluid. The flow rate is defined by the flowing volume per time unit. The flow rates are the essential control factors, in order to influence the hemofiltration. The flow rate, i.e., the strength of the flow, can be influenced by the pumps on blood or dialysate side. By the flow rates of the blood and dialysate fluid (or dialysate), the TMP is determined, i.e. the pressure that causes passing of fluid at the capillary membrane. In principle, the TMP can be calculated from the ultrafiltration rate (weight loss) and the ultrafiltration factor (pore size of the capillary membrane). More precisely and in terms of the invention, preferably the TMP can be calculated by the pressures on the blood and dialysate side, namely by $$TMP=(PB1+PB2)/2-(PD1+PD2)/2,$$

wherein PB1 is the pressure on the inlet side on blood side, PB2 is the pressure on the outlet side on blood side, PD1 is the pressure on the inlet side of the dialysate and PD2 is the pressure on the outlet side of the dialysate. Thereby the TMP can be determined through pressure measurements and followed during the treatment. According to aspects of the invention the optimal TMP can be determined by said pressure measurements and followed during the dialysis process. If it deviates too much from the optimum, the flow rate must be readjusted correspondingly. With change of the blood flow rates and dialysate, the flow rate of the required substituate fluid also changes, of course.

With respect to the substituate, the term substitution rate is correspondingly identical to the term of the flow rate. As above-described, the substitution target is predetermined by the optimal total volume which results from the substitutions rate over a specified time. By the pressure measurements on blood and dialysate side, the optimal need for substituate fluid can be determined, and under varied conditions which also are determined by pressure measurements, the need for substituate fluid can be corrected, i.e. that possibly not the optimal, but the best possible substitution target can be achieved.

Under best possible attainment or realizing the substitution target it is understood that the substitution target determined or calculated before treatment is achieved in the ideal case exactly or almost nearly depending on the given circumstances or the progress of the dialysis, if the treatment time is predetermined as fixed factor and thus cannot be changed. In other words, the optimal demand for substituate fluid determined corresponding to the determined filter identity, filter properties and the blood treatment unit, as well as optionally but preferably patient data should accurately or correspondingly to the circumstances be achieved as accurately as possible. It is thereby preferred if the substitution target is achieved to 80%, more preferably to 85%, even more preferably to 90%, even more preferably 95%, even more preferably to 96%, even more preferably to 97%, even more preferably to 98%, still more preferably to 99%, and most preferably to 100% at a given treatment time. On the other hand, instead of the treatment time the substitution target can also be defined as a given, not variable factor which has to be achieved accurately with minimum deviation from the estimated treatment time, usually with a minimum extension of the treatment time.

The present invention comprises further a method for determination of the substitution target in regard to blood treatment units in which I. at least two pressure measurement values (PB1, PB2 or PD1, PD2 or PB1, PD1 or PB1, PD2 or PB2, PD1 or PB2, PD2) are determined simultaneously or time-shifted by means of at least two pressure sensors ([PB1], [PB2] or [PD1], [PD2] or [PB1], [PD1] or [PB1], [PD2] or [PB2], [PD1] or [PB2], [PD2]), and II. based on these signals by comparison with saved data a substitution target for the next dialysis session is determined.

The pressure measurements are performed with the dialyzer and the filter which is used at the subsequent dialysis session. Moreover, these pressure measurements are performed using a reference solution before the patient is connected to the blood treatment unit.

Preferably, by the inventive method a statement can be taken how the optimal substitution target is. Moreover, it can also be detected during the dialysis session, whether disturbances occur, so that the substitution target and/or the dialysis parameters such as pressures and flow rates can be adjusted.

It is particularly preferred if at least one pressure measurement value on the blood side and at least one other pressure measurement value on the dialysate side are determined. It is further preferred if one pressure measurement value on the blood side and two pressure measurement values on the dialysate side or two pressure measurement values on the blood side and one pressure measurement value on the dialysate side are determined. In a particularly preferred embodiment, two pressure measurement values on the blood side and two pressure measurement values on the dialysate side are determined. However, it is possible and preferred, if two pressure measurement values on the blood side are measured, as a pressure pulse is spread not only through the filter membrane, but also along the membrane, and thus two values on blood side can also serve for the determination of the filter properties. The pressure measurements is performed at or directly before the inlets and outlets of the tangential flow filter TFF, herein also called dialyzer.

Detected pressure measurement values can be absolute pressures, relative pressures, absolute pressure differences between two pressure measuring points, i.e. pressure measuring sensors, relative pressure differences between two pressure measuring sensors, absolute pressure amplitudes, relative pressure amplitudes, differences between the absolute pressure amplitudes at two pressure measuring sensors or differences between the relative pressure amplitudes at two pressure measuring sensors or a combination thereof, or the frequency spectra of the pressures.

The term "absolute pressure" or "absolute pressures", as used herein, describes the pressure compared to the atmospheric pressure.

The term "relative pressure" or "relative pressures", as used herein, describes the relative change of a pressure measurement value in relation to a second pressure measurement value.

The term "pressure difference" or "pressure differences", as used herein, describes the difference of two pressures.

The term "pressure amplitude" or "pressure amplitudes", as used herein, describes the determined or measured value of the pressure fluctuations. As synonym the term pressure swing amplitude can be used.

The term "frequency spectrum" or "frequency spectra", as used herein, describes the entity of the frequencies which are generated by a swinging system or are included in a signal.

In another preferred embodiment, the determined pressure measurement values are set in relation to predetermined reference values or to previously measured initial values.

At the same time, there can be absolute or relative changes, differences in the measured values, changes in the pressure amplitudes, or the frequency spectrum. The analysis can include that the change of absolute values is monitored, particularly in relation to falling below or exceeding a tolerance range. This also includes a comparison of two absolute values, whose difference to each other, for example, should not be fallen below or exceeded a determined value. The same applies to relative changes between the two measured values, or a measured value and a reference value. In principle, this also applies to deviations in the height of amplitudes or changes in the frequency spectrum which can result from a change in the system. An exact analysis of the pressure measurement values, for example by means of an arithmetic operation, can also include an estimation of the progress of the pressure measurement value or of a trend of the pressure measurement value or of the height or the progress. For the analysis of the pressure measurement value according to aspects of the invention, each information recognizable or derivable from the signal, as well as information derivable from the measuring or determination conditions can be used. Thus, e.g. the height of the amplitude, changes in the complex amplitude of the frequencies and also in the harmonic frequencies, relative changes of two pressure measurement values to each other or shifts in the absolute values of pressure measurement values can allow a statement. This comprises among other things also the comparison of pressure measurement values of different patients or systems or treatment methods among each other. Such data and gaining knowledge there from can also be an analysis in terms of the invention.

Surprisingly, it has been found that the measurement and analysis of the pressure measurement values, e.g. generated also by a blood pump P in the system, provides information on the flow properties in a blood treatment unit. Based on this measured pressure signals at a blood treatment unit, an optimal substitution target can be determined during a dialysis. If in the process of the dialysis session disturbances occur, it can be readjusted, if necessary. According to aspects of the invention, any pressure measurement value can be used for the analysis independent on its origin. For example, in one embodiment, the pressure measurement values which are caused by the switching of a balance chamber BK, are determined and used for the analysis.

The monitoring of the system properties or of the dialysis parameters during the treatment is preferably implemented such that the pressure signals generated by the blood pump P and their propagation are monitored. According to aspects of the invention, also the pressure signals of a pump on the dialysate side or the pressure peaks generated by the switching of valves can be monitored. It is also possible to monitor combined pressure signal from both pumps, or detect each single pressure signal. Especially preferred is the monitoring of the four pressure signals at the inputs and outputs of the tangential flow filter TFF.

Depending on the system properties of the blood treatment unit, the pressure signals spread in the system along the blood flow direction and in transmembrane direction.

It is thus possible to register changes of the flow conditions by monitoring the pressure signals on the blood side and the dialysate side as well as by monitoring the ratios of these pressures and to adjust the substitution target correspondingly.

The term "blood treatment unit" refers to a device for the treatment of blood, and particularly to a device for the extracorporeal blood treatment. The term describes thereby a device that can be used for the purification and/or treatment of blood. In particular, it can be a dialysis device which is capable of hemodialysis, hemoperfusion, hemofiltration, or hemodiafiltration.

The term "system change", as used herein, comprises the interaction of components of the device for the treatment of blood, i.e. of the blood treatment unit, particularly, the filter membrane with blood. By this interaction the flow properties deteriorate both in transmembrane direction and in blood flow direction. This is caused for example by thrombocyte attachment, clotting, chemical binding of blood components to the membrane or simply mechanical (flow induced) pressing of the blood components to and even into the membrane, but is not limited to this and can also occur at other positions within the blood treatment unit. Furthermore, a system change caused by a buckled tube, leaks or a loosened connection can be detected.

The synonymous terms "system properties" or "dialysis parameters" relate to the configurations of the blood treatment unit in relation to the pressures and flow rates of blood, dialysate and substituate.

The inventive method comprises further the analysis and characterization of the flow properties in a device for the treatment of blood for the determination of the filter properties by the following steps:

a) Determining the filter properties by detecting at least two pressure measurement values by at least two pressure sensors within the blood treatment unit using a reference solution, b) Optionally comparing the detected pressure measurement values with reference values of the same patient saved on the storage unit which were detected during previous dialysis sessions or with reference values of a patient group stored on the storage unit, c) Calculating a substitution target based on the values according to step a) and optionally step b), This method is advantageous, because prior to the blood treatment, i.e. without patient, by recording of pressure measurement values with a reference solution, the properties of the used filter can be determined. If the filter properties of a specific filter type are saved on the storage unit, not only filter properties but also the specific filter type can be determined.

This is a great advantage for the patient, because nowadays transmembrane filters are mass products and such dialyzers of the dialysis wards are obtained from the currently cheapest providers and therefore a patient receives different dialyzers at different dialysis sessions. Moreover, it is too elaborating to re-optimize the substitution target manually at each dialysis session for each patient again, so that often only standard configurations are used, which are, however, usually not the best adapted substitution target for the patient. The present invention solves this problem on the one hand by determining the filter properties and a substitution target calculated there from which additionally, can be compared with available patient data. If the patient data or data of a similar patient group are stored on the blood treatment unit, so the calculation of the optimal substitution target for the patient is performed fully automatic with previous determination of the filter properties. The calculation of an optimal substitution target to be achieved at the end of the dialysis session makes only really sense, if according to such a calculation it is also guaranteed that this substitution target is also achieved at the end of the dialysis session. The blood treatment unit according to aspects of the invention enables exactly this.

The filter properties can be determined for example in terms of their differences, especially in relation to the permeability by pressure measurements (FIG. 2). Particularly, the pulse transfer and pressure level on dialysate side or TMP can give in a measurement with the reference solution information whether a filter is suitable for a HDF therapy.

With filters having low permeability, for example, the transfer in principle does not exist, i.e. here, the pulses spread only along the blood flow from PB1 to PB2, i.e. the signals are detected in principle only in the circulation on the blood side (FIG. 2C). With a filter having high permeability, the pulse spreads also through the membrane to the dialysate side, wherein the signals can be equally strong (FIG. 2A), but usually they are rather differently strong. In a stronger transfer through the membrane, the transfer along the blood flow is less.

If further on the dialysis side the performance of the ultrafiltration pump is increased, also the pressure level on dialysate side shifts; with a low-flux filter, this shift is much more distinct (FIG. 2D) than with a high-flux filter (FIG. 2B) because more energy must be expended to generate the same transmembrane flow.

In Table 1, two filters with different number of fibers are compared. The filters differ only in the number of fibers which is the result of the different membrane surfaces. Fiber geometry and permeability are otherwise identical. Here, the pressure amplitude in PB1, PB2 and PD2 is considered, as well as the relative amplitude each regarding PBE. It is critical that the larger filter which is better suitable for the HDF therapy with high volumes ensures a better impulse transfer to the dialysate side (PD2). Thus, this is also more suitable for high-volume substitution.

TABLE 1

| BF in ml/min | PB1 average | PB2 average | PD2 average | PB2/PB1 | PD2/PB1 |
|---|---|---|---|---|---|
| high-flux filter with 1.8 m² effective filter surface | | | | | |
| 100 | 27.06 | 8.63 | 12.99 | 31.9% | 48.0% |
| 200 | 52.97 | 12.17 | 18.03 | 23.0% | 34.0% |
| 300 | 87.20 | 16.12 | 26.90 | 18.5% | 30.8% |
| high-flux filter with 2.3 m² effective filter surface | | | | | |
| 100 | 22.61 | 8.12 | 12.86 | 35.9% | 56.9% |
| 200 | 45.45 | 11.32 | 18.29 | 24.9% | 40.2% |
| 300 | 79.65 | 15.85 | 28.98 | 19.9% | 36.4% |

By the storing such data as well as the used reference solution (in this case physiological NaCl-solution) filters can be compared not only relatively to each other, but also can be clearly identified, if comparison values are stored on the blood treatment unit.

By the filter properties determined in step a) by the detected pressure measurement values, the expected progress of the following blood treatment can be predetermined with a known filter, or also an unknown filter. This is advantageous because prior to the beginning of dialysis without the need for a test run with patient's blood, the optimal volume of required substitution fluid corresponding to the filter properties can be determined as the substitution target. This step is also advantageous because also individual filters of the same type can differ in regard to their filter-specific properties and can lead to different dialysis progresses. Furthermore, this step is also advantageous because in reuse of the same filter even with thoroughly cleaning of the filter substantial properties can be changed, wherein a reuse is practiced currently only in the United States.

Thereby step a) comprises preferably the individual steps a1) Detecting pressure measurement values within the blood treatment unit using a reference solution, and a2) determining the filter properties by comparing the pressure measurement values detected in step a1) with pressure measurement values stored on the storage unit.

Step a2) can be carried out also by comparison with pressure measurement ranges of specific filter types stored on the storage unit in order to determine not only the filter properties, but also the specific filter type. If no pressure measurement values of specific filter types are stored, thus, we compare pressure measurement values detected according to step a1) with saved pressure measurement values which represent the filter properties, so that from this comparison the filter properties can be determined.

The pressure measurement values detected in step a) can also serve for the identification of a specific filter type, if the filter-specific properties are stored or saved on the storage unit of the blood treatment unit. A dialysis filter is characterized by filter-type properties such as total size, number of hollow fibers or tubes, surface size and sieving coefficient. These characteristics cause a specific flow behavior of the reference fluid which is recognized by defined pressure measurement values. Accordingly, the filter can be identified. This identification is advantageous because thereby empirically detected filter-specific values can be used, which were detected during treatments that operated very well. Thus, the substitution target can be determined on the basis of the detected filter type. The inventive method then comprises the following steps:

a) Determining the filter properties by detecting at least two pressure measurement values by at least two pressure sensors within the blood treatment unit using a reference solution and comparison with filter-related pressure measurement values stored on the storage unit;
b) Optionally comparing the pressure measurement values detected in step a) with reference measurement values of the same patient stored on the storage unit which were recorded in previous dialysis sessions or with reference values of a patient group stored on the storage unit;
c) Calculating a substitution target based on the values according to step a) and optionally step b);

In regard to the reference values of a patient group, it is preferably a patient group similar to the patient to be treated, so that an averaged value which is also applicable to the patient to be treated results from this similar patient group.

By comparing the measured values in step b) with patient data stored on the storage unit, i.e. by comparison with values from especially good treatments the substitution target can be determined optimal corresponding to the used filter and the treated patient or with respect to a patient group. Thus, it is possible to refer to values of one and the same patient from a single treatment which was well to optimal, preferably however, to averaged values from treatments being as well as possible. Averaged values are understood here as averages of the treatment processes. The averaged values form thus an expected value for the further or coming treatment. Preferably, the data from previous dialysis processes are weighted, i.e. that certain dialysis processes are evaluated differently in terms of their importance or significance or in the light of local and temporal differences, such as filter type or blood treatment unit or duration of dialysis.

By comparing with stored values of specific patient groups it goes back to values of similar type patients. Under similar type patients, patients are understood with similar blood test results, similar renal dysfunction, approximately the same age, weight and sex, as well as similar treatment history. Here, the data are averaged and preferably also weighted.

Accordingly, the optimal substitution target can be determined as above-described.

The detection of the pressure measurement values is performed via pressure sensors. For this, the pressure sensors known from the prior art can be used, such as piezoresistive, piezoelectric, frequency-analog, pressure sensors with hall elements, capacitive, inductive and/or combinations thereof. Preferred are pressure sensors whose sampling rate is preferably at least 20 Hz. The sampling rate describes here the rate the signal values are taken from a continuous signal.

The detected pressure measurement data can be used for classification of the filtration potential of the blood treatment unit. For this, the measured values can be assigned to the corresponding classification groups stored on the storage unit. Each classification group corresponds to an instruction, how, if necessary, the substitution target is to be adjusted. Such an instruction can be proposed to the operator by a display or can be automatically implemented at the dialyzer.

Alternatively, a defined ultrafiltration value can be assigned to a specific measured filtration potential.

According to aspects of the invention at least one pressure sensor, preferred two pressure sensors, more preferred three pressure sensors and most preferred four pressure sensors is used. According to aspects of the invention, if needed, also further pressure sensors can be used The inventive connections are presented in details in the following:

The transmembranous initial situation can be detected by determining the ratio of the pressure measurement values, for example, that of the amplitudes ($A_i$), at the pressure sensors [PD2] and [PB1]. This parameter is monitored and optionally in case of falling below or exceeding a defined value (once or over a defined time period), a countermeasure is proposed or initiated automatically.

A decreasing permeability of the filter membrane is reflected on the one hand in a reduction of the ratio of $A_{PD2}/A_{PB1}$ and on the other hand due to the conservation of momentum also an increase of $A_{PB2}/A_{PB1}$ is caused.

The flow resistance on blood side can be detected from the difference of the detected pressure measurement values from PB1 and PB2, and/or the ratio from PB1 and PB2, and/or the change of the pressure amplitude $A_{PB1}$ and/or the change of the pressure amplitude $A_{PB2}$ and/or the ratio of the pressure amplitudes $A_{PB1}$ and $A_{PB2}$ and serves as indicator of the flow resistance on blood side. One or more of these parameters are monitored and in case of falling below or exceeding a defined value, a countermeasure can be proposed or initiated automatically.

A constriction in the circulation on blood side, e.g. by clotting in the filter or in the patient's recirculation, causes depending on position of the constriction to a characteristic shift of the ratios from PB1 and PB2. If it is located for example, between the two measuring points, thus the pressure difference of these two values increases, if it is located behind them, a parallel increase of both values occurs.

The transmembrane flow resistance is detected from the difference of the detected pressure measurement values from PB1 and PD2, and/or the ratio from the PB1 and PD2, and/or the difference from the PB2 and PD2, and/or the ratio from the PD2 and PB2. Furthermore, changes of the pressure amplitude $A_{PD2}$ and/or the ratio of the pressure amplitudes $A_{PB1}$ and $A_{PD2}$ and/or the ratio of the pressure amplitudes $A_{PB2}$ and $A_{PD2}$ and/or the difference from PB1 and PD1 and/or the ratio from the PB1 and PD1 and/or the difference from PB2 and PD1 and/or the ratio from the PB2 and PD1 and/or the change of the pressure amplitude $A_{PD1}$ and/or the ratio of the pressure amplitudes $A_{PB1}$ and $A_{PD1}$ and/or the ratio of the pressure amplitudes $A_{PB2}$ and $A_{PD1}$ serve as indicator for the transmembrane flow resistance.

Similarly, $A_{PB1}$, $A_{PD1}$ or $A_{PD2}$ or a combination thereof can be used as indicator for the permeability of the filter membrane and filter surface.

Further, PB1 and PB2 or the pressure amplitudes of PB1 and PB2 can be used as indicator for the flow resistance of the filter.

Accordingly, the determined pressure measurement data can be used for calculating the permeability, the permeable surface, and the flow resistance of the filter.

A consequence can be for example that at an increased resistance in the blood flow direction and at the associated reaching of the limit values of pressure measurement values on blood side, rinsing with a saline solution, an increase of the rinsing rate, a stronger hemodilution, or a change of the blood flow, or a combination thereof is proposed or initiated.

If there is a coincidence of an increased flow resistance on blood side with an increase of the hematocrit of the patient, for example, the increase of the dosage of the blood-thinning or anticoagulant agent can be proposed or initiated. In the reverse case, such as a coincidence of decreased flow resistance on blood side with a low hematocrit of the patient, reduction of the dosage of the blood-thinning or anticoagulant agent can be proposed or initiated.

[PB1] designates the pressure sensor in the blood circulation before the blood inlet into the tangential flow filter TFF and PB1 designates the pressure measured at the pressure sensor [PB1]. [PB2] designates the pressure sensor in the blood circulation behind the blood outlet from the tangential flow filter TFF and PB2 designates the pressure measured at the pressure sensor [PB2]. [PD1] designates the pressure sensor in the dialysate circulation before the dialysate inlet into the tangential flow filter TFF and PD1 designates the pressure measured at the pressure sensor [PD1]. [PD2] designates the pressure sensor in the dialysate circulation behind the dialysate outlet from the tangential flow filter TFF and PD2 designates the pressure measured at the pressure sensor [PD2].

Previous approaches could not differentiate between changes in blood flow direction, dialysate flow direction and transmembrane direction, whereby a targeted elimination of disturbances was not available. By the use of up to four pressure sensors and the analysis of the detected pressure measurement values at each of these pressure sensors, all above-mentioned circumstances can be monitored. Using the entity of the pressure measurement values, a complete analysis can be performed, which enables to determine the type of the system change specifically. By a suitable analysis of four pressure measurement values also the position of the disturbance is at least localized.

Preferably, the pressure measurement values are detected on blood side at the pressure sensor [PB1] as well as at the pressure sensor [PB2]. On dialysate side, the pressure measurement values are detected preferably at the pressure sensor [PD2] and at the pressure sensor [PD1].

In an alternative embodiment, it is however sufficient if the pressure measurement values PB1 and PB2 and one of the signals PD1 or PD2 on dialysate side is available.

Furthermore, the pressure PD1 or PD2, or both together can be observed during transmembrane flushing depending on the rate of the flushing flow.

The analysis is performed by the comparison of at least two or more pressure measurement values such that this are here the absolute pressures and/or the relative pressures and/or the pressure differences and/or the pressure amplitudes and/or the difference of the pressure amplitudes and/or the relative pressure amplitudes and/or the frequency spectra. For the analysis, changes of the detected pressure measurement values compared to predetermined reference values and/or changes to previously measured initial values are detected. The can be absolute and/or relative changes, differences in the measured values, changes in the pressure amplitudes and/or the frequency spectrum. Analyzable are here all the information that are derived from the detected data, in particular the height of the amplitudes, averaged values, trends, integrals, differentials, delays of pressure fluctuations, fluctuations, coupling degree or correlation degree, distribution of signals, etc.

The analysis of the detected pressure measurement values is performed using devices which are known to the person skilled in the art from prior art, the devices are preferably a storage unit and a central processing unit. The central processing unit can comprise, e.g. for the analysis of the measured data, a CPU which calculates changes of the measured pressure measurement values compared to predetermined reference values and/or changes to previously measured initial values. The analysis can be performed in the form of absolute and/or relative changes, differences in the measured values, changes in the pressure amplitudes, e.g. the height of the amplitudes and/or the frequency spectrum.

If the measured pressure measurement values at the at least two pressure sensors selected from the group consisting of [PB1], [PB2], [PD1] and [PD2] result in that the measured pressure measurement values deviate from the reference pressure measurement values over a tolerance interval, it follows that the dialysis parameters, namely the flow rates of blood, dialysate and/or substituate must be adjusted. The reference pressure measurement values are pressure measurement values which have been obtained in dialysis sessions the substitution target has been achieved. If therefore the pressure measurement values are compared with the stored reference pressure measurement values taking into account a possibly different transmembrane filter and/or a possibly changed patient constitution, it can be predicted from the comparison whether the calculated substitution target will be achieved.

Under adjustment of the flow rate of blood, dialysate and/or substituate is understood an adaptation to changed conditions within the blood treatment unit in order to come closest to the calculated substitution target, if the treatment time is defined or to change the given treatment time as little as possible, if the substitution target is defined. Thereby it is preferred, if the corresponding undertaken changes are not performed abruptly, but slowly or even delayed. This gradual adjustment is advantageous because slow increases of the substitution rate affect, for example, the formation of the secondary membrane advantageously. By too abrupt flow rate changes, also disturbances in the system could occur. Here, the adjustment can be done preferably by a slow increase or also decrease of the blood flow rate, or the dialysate flow rate. However, an increase does not cause necessarily always a better achievement of the substitution target; at an increase beyond a defined limit value, for example, the transmembrane pressure of the filter membrane can be decreased and thus, the filtration efficiency decreases. Therefore it is also preferred to reduce the flow rate, if necessary.

The adjustment can be performed automatically by the system, if a corresponding control program is stored on the central processing unit. The changes detected via the pressure sensors are compared with stored values and control orders are issued for the adjustment of adjustable system parameters, e.g. the flow rates in order to achieve the calculated substitution target at the best. In doing so it is preferred, if the system provides in regard to control steps for the adjustment to changed conditions an acoustic signal via a speaker and/or visual signal via the display.

It is furthermore preferred that another signal sounds, if within a defined time period, an adjustment was carried out several times. This warning signal sounds preferably in regard to more than three adjustments within an hour, more preferably within half an hour, and more preferably within 10 minutes. The issue of this warning signal is advantageous because the dense sequence of necessary adjustments to system changes can be, as described above, for example, buckled tubes or blockages or leaks in the system can indicate. For the inspection and elimination of these disturbances the intervention of trained personnel or professionals would be necessary here. But if such extraordinary disturbances of the blood treatment unit does not exist, necessary adjustments of the flow rates can be indicated, or also can be made by the blood treatment unit automatically to achieve the substitution target in an optimal way within the predetermined treatment time, or to deviate from the estimated treatment time as little as possible, particularly to extend this as little as possible, if the substitution target is defined as a given value.

The adjustment can be performed on the basis of values provided via the monitor also by trained personal. Also here the above-mentioned conditions for the gradual adjustment apply.

In a preferred embodiment, the analysis of the pressure measurement values is performed on a central processing unit. This central processing unit comprises a preferably a CPU, an input for the pressure measurement values, and a display for the pressure measurement values and/or the determined recommendations to act. In a particularly preferred embodiment, the central processing unit includes additionally an output via which the substitution target determined and adjusted to the disturbances is automatically forwarded to the dialysis machine and the determined adjustment is carried out automatically on the dialysis machine.

The effectiveness of the blood treatment depends primarily on four factors: the treatment time, the blood flow, the clearance and the dialysate flow. Especially, the sufficiently long treatment time must be guaranteed and is a major factor for a successful treatment. Numerous studies have shown that the higher the administered dialysis dose, the lower the patient mortality is (over a broad correlation range).

Disturbances to be eliminated on-site by the staff in charge accumulate quickly to several incidents per year. In the extreme case, sessions must be even canceled. Far more often, however, are the cases in which a disturbance is not detected and therefore is not eliminated, which causes a suboptimal dialysis result. By a directed elimination of disturbances, these timeouts are reduced to a minimum and can be avoided in some cases completely by initiating the proper measure on-site. The search for the reason of the disturbance is omitted as far as possible and thus it gives the patient an increased sense of security. Consequently, the dialysis efficiency is increased and also the cost-effectiveness of dialysis increases.

The pressure measurement values determined during the treatment are compared by the central processing unit with the reference pressure measurement values determined at the beginning using the reference solution and with the reference pressure measurement values which were determined during other treatments. In case of the deviation of at least one measured value from the corresponding reference pressure measurement value, an adjustment of the flow rates is performed. This adjustment can be performed by the changes, i.e. increase or decrease, of the blood flow rate, dialysate or substituate fluid, particularly preferably of the substituate fluid (herein also called only substituate). The treatment time remains thereby constant. It is further preferred if in case of given treatment time the flow rates are changed so that the given substitution target can be realized in an optimal way.

It is further also preferred if the defined substitution target is achieved by changing, preferably extending, the treatment time and remaining the flow rates constant, wherein it is particularly preferred if the treatment time is changed as little as possible.

The term "flow properties" as used herein, refers to the entity of the properties of each of the flowing fluids. Of particular interest are the dynamic viscosity, the flow rate, the flow volume, the flow profile, osmotic pressure, the surface tension as well as the changes and artifacts generated by the used pumps as well as by the other active operating elements such as electric devices and passive operating elements such as the tube system and the dialyzer.

The term "ratio" as used herein, is not necessarily limited to the quotients from two values, but can also comprise the difference or any other parameter the "ratio" between two values may be expressed.

In one embodiment, the relative change of individual measuring points over the time $A_{PDi}(t)/A_{PDi}(t=0)$ or $A_{PBi}(t)/A_{PBi}(t=0)$ is a suitable control parameter.

Relative measurements of the above-mentioned parameters provide the advantage that the influence of different blood flows as well as return flow resistances is dropped.

The analysis of the frequency spectrum of individual pressure measurement values has further shown that a change of the permeability affects the amplitude of the harmonic frequencies. The same applies to flow changes in blood flow direction.

In a preferred embodiment, the frequency spectrum of individual signals and the relative change is determined in relation to a second signal. By analysis of the two frequency spectra, a statement about the flow properties in blood flow direction, dialysate flow direction or in transmembrane direction can be made, wherein blood flow direction and transmembrane direction are preferred.

Preferred is thereby the measurement of at least two pressure measurement values in the blood treatment unit using at least two pressure sensors, i.e. at least one pressure measurement value per pressure sensor.

Furthermore, the present invention relates to a method for the best possible achievement of a defined substitution target in a blood treatment unit which comprises the following steps:

a) Determining the filter properties by detecting at least two pressure measurement values by at least two pressure sensors within the blood treatment unit using a reference solution, b) Optionally comparing the detected pressure measurement values with reference values of the same patient which were recorded during previous dialysis sessions or with reference values of a patient group, c) Calculating the substitution target based on the values according to step a) and optionally step b), d) Measuring of pressure measurement values by at least two pressure sensors during a blood treatment, e) Comparing the pressure measurement values detected according to step d) with reference pressure measurement values, and f) Adjusting the flow rate of blood, dialysate and/or substituate in case of deviation of at least one detected pressure measurement value from the reference pressure measurement value in order to achieve the substitution target during the defined treatment time in an optimal way or to change the treatment time for a given substitution target as little as possible.

Another embodiment of the present invention relates to a method for an optimal attainment of a calculated substitution target using a blood treatment unit with a dialyzer, at least two pressure sensors, a central processing unit and a storage unit, wherein the method comprises the following steps:

a) Determining the filter properties by detecting at least two pressure measurement values at the at least two pressure sensors within the blood treatment unit using a reference solution, b) Optionally comparing the detected pressure measurement values with reference values of the same patient saved on the storage unit which were recorded during previous dialysis sessions or with reference values of a patient group saved on the storage unit, c) Calculating the substitution target based on the values according to step a) and optionally step b), d) Measuring of pressure measurement values at the at least two pressure sensors during a blood treatment, e) Comparing the pressure measurement values detected according to step d) with reference pressure measurement values saved on the storage unit, and f) Adjusting the blood flow rate, dialysate and/or substituate in case of deviation of at least one detected pressure measurement value from the reference pressure measurement value saved on the storage unit in order to achieve the substitution target for a given treatment time in an optimal way or to change the treatment time for a given substitution target as little as possible.

As reference pressure measurement values preferably serve those which have been recorded during a blood treatment or during blood treatments, in which the substitution target has been achieved.

In regard to the comparison of the detected pressure measurement values with the reference pressure measurement values saved on the storage unit, it is self-evident that the pressure measurement values detected at the same pressure sensor and at approximately the same time during the blood treatment are compared with each other.

Thereby in all embodiments of the inventive method and the inventive blood treatment unit, following formulations of step f) are also possible:
- f) Adjusting of the flow rate(s) of blood or dialysate or substituate or of blood and dialysate or dialysate and substituate or blood and substituate or of blood and dialysate and substituate in case of deviation of at least one detected pressure measurement value from the corresponding reference pressure measurement value in order to achieve the substitution target during a given treatment time in an optimal way or to change the treatment time for a given substitution target.

or
- f) Adjusting of the flow rate of blood or dialysate or substituate or the flow rate of blood and dialysate or dialysate and substituate or blood and substituate or blood and dialysate and substituate in case of deviation of at least one detected pressure measurement value from the corresponding reference pressure measurement value saved on the storage unit in order to achieve the substitution target during defined treatment time at the best or to change the treatment time for a defined substitution target.

In all embodiments of the inventive method, the stored reference pressure measurement values can have been recorded according to step e) in regard to blood treatments the substitution target has been achieved during the treatment time.

In another preferred embodiment of the inventive method, the data with which is compared, are saved on a storage unit and the necessary adjustments and corresponding control signals are provided by a central processing unit. The inventive method for an optimal attainment of a given substitution target by a blood treatment unit with a dialyzer, at least two pressure sensors, a central processing unit and a storage unit, comprises then the following steps:
- a) Determining the filter properties by detecting at least two pressure measurement values at the at least two pressure sensors within the blood treatment unit using a reference solution,
- b) Optionally comparing the detected pressure measurement values with reference values of the same patient saved on the storage unit which were detected during previous dialysis sessions or with reference values of a patient group saved on the storage unit,
- c) Calculating the substitution target based on the values according to step a) and optionally step b),
- d) Measuring of pressure measurement values at the at least two pressure sensors during a blood treatment,
- e) Comparing the pressure measurement values detected according to step d) with reference pressure measurement values saved on the storage unit, and
- f) Issuing a signal indicating the necessity of the adjustment or automatically adjusting of the flow rate of blood, dialysate and/or substituate in case of deviation of at least one detected pressure measurement value from the corresponding reference pressure measurement value saved on the storage unit in order to achieve the substitution target during the given treatment time in an optimal way or to change the treatment time for a given substitution target as little as possible.

The measurement of the pressure values can be performed simultaneously or time-shifted in all embodiments of the inventive method and the inventive device.

In the inventive method, it is preferred if in step c) at least two simultaneous pressure measurement values which are measured using at least two of the pressure sensors ([PB1], [PB2], [PD1] and [PD2]), are used for the calculation of the substitution target.

In the inventive method, it is further preferred if in step c) at least two time-shifted pressure measurement values which are measured at least at one of the pressure measuring sensors ([PB1], [PB2], [PD1] and [PD2]), are used for the calculation of the substitution target.

In the inventive method, it is further preferred if in step c) the blood flow, the hematocrit of the patient, the total protein concentration of the patient or the patient history or a combination thereof are included in the determination of the optimal substitution target.

In the inventive method, it is further preferred if in step c) the patient history is included so that for the case that in regard to a substitution target determined as optimal for at least one previous dialysis session complications have been occurred for one patient, the optimal substitution target determined for the following dialysis session is reduced to this value recognized as critical, if it is equal to or greater than this critical value.

Further, it is preferred if the duration of the blood treatment, i.e. the time of the dialysis session, is determined and the calculated substitution target is achieved within the given duration in an optimal way. This ensures a trouble free process in the dialysis wards and the best possible result for the patient.

More preferred is the measurement of pressure measurement values at three pressure sensors in a blood treatment unit with a dialyzer, at least three pressure sensors, a central processing unit, and a storage unit.

Particularly preferred is the measurement of pressure measurement values at four pressure sensors in a blood treatment unit with a dialyzer, at least four pressure sensors, a central processing unit and a storage unit. Thus, the present invention relates also to a blood treatment unit with a dialyzer, at least four pressure sensors, a central processing unit, and a storage unit adapted to perform the following procedure:
- a) Determining the filter properties by detecting at least four pressure measurement values at the at least four pressure sensors within the blood treatment unit using a reference solution,
- b) Optionally comparing the detected pressure measurement values with corresponding reference values of the same patient saved on the storage unit which were detected during previous dialysis sessions or with reference values of a patient group saved on the storage unit,
- c) Calculating a substitution target based on the values according to step a) and optionally step b),
- d) Measuring of pressure measurement values at the at least four pressure sensors during a blood treatment,
- e) Comparing the pressure measurement values measured according to step d) with corresponding reference pressure measurement values saved on the storage unit, and
- f) Adjustment of the flow rate of blood, dialysate and/or substituate in case of deviation of at least one detected pressure measurement value from the corresponding reference pressure measurement value saved on the storage unit in order to achieve the substitution target for a given treatment time in an optimal way or to change the treatment time for a given substitution target as little as possible.

As used herein, the expression "of four pressure measurement values at four pressure sensors" means that a pressure measurement value is measured per pressure sensor, i.e. overall 4 pressure measurement values are obtained and not that at each of the 4 pressure sensors 4 pressure measurement values are measured, i.e. overall 16 pressure measurement values are obtained. The same applies to the term "of (at least) three pressure measurement values at (at least) three pressure sensors", where overall i.e. (at least) three pressure measurement values are obtained (namely one per pressure sensor) and also for the term "of (at least) two pressure measurement values at (at least) two pressure sensors", where overall i.e. (at least) two pressure measurement values are obtained.

If the blood treatment unit has four pressure sensors, one is located at the inlet of the dialyzer on dialysate side [PD1] and the second is located at the outlet of the dialyzer on dialysate side [PD2] and the third is located at inlet of the dialyzer on blood side [PB1] and the fourth is located at the outlet of the dialyzer on blood side [PB2].

If the blood treatment unit has three pressure sensors used according to aspects of the invention, thus, one of the four aforementioned pressure sensors [PD1], [PD2], [PB1] and [PB2] is missing. If the blood treatment unit has two pressure sensors used according to aspects of the invention, thus, two of the four aforementioned pressure sensors [PD1], [PD2], [PB1] and [PB2] are missing.

In another embodiment of the method, the pressure signals of a blood pump are used for the inventive differentiation of system changes.

In another embodiment, the pressure signals of a balance chamber BK are detected for the inventive differentiation of system changes.

A preferred embodiment of the method comprises further the step correct the pressure measurement values by external influence parameters. The term "external influence parameters" as used herein comprises flow rates, height change of the patient inlet or increased resistance in the patient's return flow. With height change is meant that the patient changes his spacial position in the comparison to the tangential flow filter TFF. Another important influence factor is the blood pressure of the patient. Thus, for example, hypotension occurs relative often. For the compensation of such changes the relative values can be considered. If the individual signals show changes that suggest a change of external influences, this signal is characterized as "critical" for the time period of the change and in doubt is not used for the analysis. The same procedure is used when signals on blood and dialysate side are set in relation to each other.

An embodiment for the detection of pressure measurement values for the inventive differentiation of system changes comprises the following steps:
  (a) At least two pressure measurement values are detected in a blood treatment unit simultaneously or time-shifted,
  (b) correction of the pressure measurement values from external influence parameters,
  (c) analysis of the at least two corrected pressure measurement values from (b) for making a statement about the flow properties in blood flow direction or in transmembrane direction.

It can be put not only the signals of two different pressure sensors into the relation to each other, but also the chronological sequence of a signal. As an example, monitoring of the amplitude on the dialysate side may be mentioned. If the amplitude is smaller, either the permeability of the membrane or the effective membrane surface has been reduced, or the input signal has become weaker. Here, however, no offset correction can be considered. External influences would be reflected directly in the measurement results. By a relative assessment in comparison to the amplitude of the input signal and with a simultaneous monitoring of the output, on blood side, the problem, however, is identified very precisely.

In all methods described herein, it is preferred to detect more than two pressure measurement values and in particular 4 pressure measurement values simultaneously or time-shifted at the inlets and outlets of the tangential flow filter TFF such as made by the pressure sensors [PB1], [PB2], [PD1] and [PD2].

The invention comprises further also a device for the measurement of pressure measurement values in a device for the treatment of blood which increases the dialysis efficiency and economic efficiency of dialysis, by differentiation between system changes which occur in blood flow direction or in transmembrane direction, comprising at least one pressure sensor for the measurement of pressure measurement values.

All above-described embodiments and advantages relate advantageously also to the method and the device for detection of pressure measurement values in a blood treatment unit which increases the dialysis efficiency and economic efficiency of the dialysis and also ensures that the volume of substituate solution corresponding to the respective performance of the dialysis machine is supplied to the patient. This serves also for the safety of the patient and his physical well-being during and after the respective dialysis session.

The composition of the pressure measurement values is not significant for the inventive method. According to aspects of the invention, pressure measurement values from individual sources can be used, but also pressure measurement values which are composed of a plurality of sources.

In some embodiments, it may be advantageous if only one value from the sum of the pressure measurement values is determined or only one is filtered out from the sum of the pressure measurement values in order to determine a valid value for the other pressure measurement values. This can e.g. be the case, if a very irregular pressure measurement value would superimpose the measurement of the other, or if a specific pressure signal is due to its properties, particularly suitable for the measurement. Such configurations for the correction of the pressure measurement values are well known from the prior art.

In summary, the inventive method for determining and optimal realizing the substitution target using blood treatment units comprising a dialyzer, at least two pressure sensors, a central processing unit and a storage unit may be represented by the following steps:
  a) Determining the filter properties or the filter type by detecting pressure measurement values within the blood treatment unit using a reference solution;
  b) Comparing the detected pressure measurement values with corresponding measurement values saved on the storage unit;
  c) Determining the substitution target based on the information according to step a) and optionally step b);
  d) Measuring of pressure measurement values in a blood treatment unit during a blood treatment;
  e) Comparing of the detected pressure measurement values with corresponding reference pressure measurement values saved on the storage unit; and f) In case of deviation of at least one detected pressure measurement value from the reference pressure measurement value, adjustment of the flow rate(s) and/or the pressure/the pressures of blood, dialysate and/or substituate in order to achieve the substitution target during a given treatment time in an optimal way or to change the treatment time for a given substitution target as little as possible, wherein the central processing unit is configured to identify specific filter properties on the basis of the pressure measurement values detected using the reference solution, and to determine an optimal substitution target corresponding to the identified filter properties before the beginning of a treatment and to detect pressure measurement values during the blood treatment and to compare with reference pressure measurement values and to generate control signals in case of deviations in order to propose or perform the adjustment of the flow rate(s) and/or the pressure/the pressures of the blood, dialysate and/or substituate in order to achieve the substitution target during a given treatment time in an optimal way, or to change the treatment time for a given substitution target as little as possible.

The present invention comprises further a device according to aspects of the invention for the detection of pressure measurement values in a blood treatment unit in order to measure system changes in filtration processes and to differentiate between system changes which occur in blood flow direction or in transmembrane direction, comprising at least two pressure sensors for the detection of pressure measurement values.

The inventive blood treatment unit is preferred a device for the extracorporeal blood treatment with a dialyzer (tangential flow filter TFF) which is separated by its semipermeable membrane (11) into a first and a second chamber, wherein the first chamber (12) is arranged in a dialysate way and the second chamber (13) is connectable by means of a blood supply (14) and a blood discharge (15) with the blood circulation of a patient (☺), an inlet (20) for fresh dialysate, an outlet (30) for spent dialysate, a pump in the blood supply between patient inlet (☺) and TFF, as well as a balance chamber (BK) and an ultrafiltration pump (UFP) in the dialysate way (FIG. 1).

In the blood treatment unit, at least one, preferably at least two, also preferably at least three and most preferably at least four pressure sensors can be attached. Thereby, the definition and arrangement of the pressure sensors is as follows: [PB1] is the pressure sensor on the inlet side of the TFF on blood side or in the blood supply (14), [PB2] is the pressure sensor on the outlet side of the TFF on blood side or in the blood discharge [15], [PD1] is the pressure sensor on the input side of the dialysate of the TFF or the inlet for fresh dialysate (20) and [PD2] is the pressure on the output side of the dialysate of the TFF or the outlet for spent dialysate (30).

In a preferred embodiment, a pressure, sensor [PB1] between a pump P and a filter TFF and another pressure sensor [PB2] between the filter TFF and the patient are attached on blood side and a pressure sensor [PD2] behind the outlet of the filter TFF and another pressure sensor [PD1] before the inlet into the filter TFF are attached on dialysate side.

In another embodiment, the inventive device comprises further a device for the analysis of the measured data. This can preferably be a storage unit and/or a central processing unit, e.g. a CPU which calculates changes of the detected pressure measurement values in regard to predetermined reference values and/or changes to previously detected initial values In further embodiments, the inventive device comprises only one pressure sensor. A statement about a system change in the filtration process is made based on the chronological development of the measurement values of this one pressure sensor. This pressure sensor can be [PB1], [PB2], [PD1] or [PD2].

In table 2 exemplarily some model constellations for pressure changes occurring in the operation of a dialysis machine and the underlying disturbances are summarized:

TABLE 2

| PB1 | PB2 | PD1 | PD2 | Disturbance |
|---|---|---|---|---|
| − | 0 | 0 | 0 | Blocking is reduced |
| − | 0 | 0 | 0 | Reduction of the UF rate reduces the hemoconcentration |
| −− | −− | −− | −− | Acute flow constriction before PD1 |
| −− | −− | 0 | −− | Acute flow constriction between PD1 and filter |
| + | 0 | 0 | 0 | lower flow area for the blood caused by clotting |
| + | 0 | 0 | 0 | Increase of the UF rate results in a stronger hemoconcentration |
| + | 0 | − | − | Secondary membrane formation |
| + | + | + | + | Pressure level on patient side increases (e.g. higher input hematocrit, change of the arm position) |
| + | + | + | + | Flow change in the inlet |
| ++ | 0 | 0 | 0 | Problems on the tube system between PB1 and filter |
| ++ | 0 | ++ | ++ | Problems on the tube system between filter and PB2 |
| ++ | ++ | ++ | ++ | Problems on the tube system behind PB2 or flow change in the access |
| 0 | 0 | 0 | −− | Acute flow constriction between filter and PD2 |

+ increases
++ increases strongly (fast)
− decreases
−− decreases strongly (fast)
0 remain unchanged By clotting exemplarily the effective membrane surface can be reduced. Consequently, the pressures on dialysate side decrease in order to maintain the UF rate. Accordingly, an increase of PB1 can result in that PD1 and PD2 decrease similarly, since the balancing must be maintained and therefore the same flow, passes through a reduced area.

A preferred embodiment comprises the device for the treatment of blood, a tangential flow filter TFF, a pump P, and at least two pressure sensors ([PB1], [PB2] or [PD1], [PD2] or [PB1], [PD1] or [PB1], [PD2] or [PB2], [PD1] or [PB2], [PD2]), wherein the pressure sensors ([PB1], [PB2] or [PD1], [PD2] or [PB1], [PD1] or [PB1], [PD2] or [PB2], [PD1] or [PB2], [PD2]) are directly upstream to the tangential flow TFF and/or directly downstream.

In another preferred embodiment, the device for the treatment of blood comprises a tangential flow filter TFF, a pump P, and at least three pressure sensors ([PB1], [PB2], [PD1] or [PB1], [PB2], [PD2] or [PD1], [PD2], [PB1] or [PD1], [PD2], [PB2]), wherein the pressure sensors ([PB1], [PB2], [PD1] or [PB1], [PB2], [PD2] or [PD1], [PD2], [PB1] or [PD1], [PD2], [PB2]) are directly upstream to the tangential flow TFF and/or directly downstream.

More preferred is a device for the treatment of blood comprising a tangential flow filter TFF, a pump P, and four pressure sensors [PB1], [PB2], [PD1] and [PD2], wherein the pressure sensors [PB1], [PD1] are directly upstream to the tangential flow filter TFF and the pressure sensors [PB2], [PD2] are directly downstream to the tangential flow filter TFF.

The present invention relates preferably to a blood treatment unit with a dialyzer and at least two pressure sensors adapted to carry out the following method:
  a) Measuring of at least two pressure measurement values at the at least two pressure sensors within the blood treatment unit using a reference solution,
  b) Determining the filter properties or the filter type by comparing the pressure measurement values detected in step a) with saved corresponding pressure measurement values of a filter sort or a filter type,
  c) Calculating a substitution target based on the information according to a) and b),
wherein specific filter properties can be identified on the basis of the pressure measurement values detected by means of the reference solution, and an optimal substitution target can be determined corresponding to the identified filter properties before the beginning of a treatment.

The device is therefore, suitable to determine the properties of the used filter, or even to identify the filter type if type-specific data are stored at initial startup of the blood treatment unit by recording pressure measurement values, and to make correspondingly a prediction about the optimal substitution target, thus, to determine the amount of substitute fluid needed under best possible conditions. Here, the stored measurement values serve for the comparison with the current measurement values and thus serve for the determination of the substitution target or for statements about the condition of the system and/or the filter.

The present invention relates also preferred to a blood treatment unit with a dialyzer and at least two pressure sensors adapted to perform the following method:
  a) Determining the filter properties by detecting at least two pressure measurement values by at least two pressure sensors within the blood treatment unit using a reference solution,
  b) Optionally comparing the detected pressure measurement values with reference values of the same patient saved on the storage unit which were detected during previous dialysis sessions or with reference values of a patient group saved on the storage unit,
  c) Determining a substitution target based on the values measured according to step a) and optionally step b),
  d) Recording of at least two pressure measurement values at the at least two pressure sensors during blood treatment,
  e) Comparing the pressure measurement values with saved reference pressure measurement values; and
  f) Adjusting the flow rate(s) of blood, dialysate and/or substituate in case of deviation of at least one detected pressure measurement value from the reference pressure measurement value in order to achieve the substitution target determined in step c) during the defined treatment time in an optimal way or to change the treatment time with adhering to the given substitution target,
wherein specific filter properties can be identified on the basis of the pressure measurement values detected using the reference solution, and a best possible substitution target can be determined corresponding to the identified filter properties before starting a treatment. The system is further so configured that it can detect pressure measurement values during a blood treatment, compare them with reference pressure measurement values and generate control signals in case of deviations in order to achieve the substitution target at the best.

In all embodiments of the inventive blood treatment unit, the saved reference pressure measurement values can be detected according to step e) during blood treatments in which the substitution target has been achieved during the treatment time.

It is in the terms of the invention also particularly preferred if a storage unit and a central processing unit are components of the blood treatment unit. The present invention, therefore relates particularly preferred to a blood treatment unit with a dialyzer, at least two pressure sensors, with at least one storage unit and at least one central processing unit adapted to perform the following method:
  a) Determining the filter properties by detecting at least two pressure measurement values by at least two pressure sensors within the blood treatment unit using a reference solution,
  b) Optionally comparing the detected pressure measurement values with reference values of the same patient saved on the storage unit which were detected during previous dialysis sessions or with reference values of a patient group saved on the storage unit,
  c) Calculating a substitution target based on the values according to step a) and optionally step b),
wherein the storage unit is configured to identify specific filter properties on the basis of the pressure measurement values measured using the reference solution, and to determine a best possible substitution target corresponding to the identified filter properties before starting a treatment.

The invention relates further particularly preferred to a blood treatment unit with a dialyzer, at least two pressure sensors, with at least one storage unit and at least one central processing unit adapted to perform the following method:
  a) Determining the filter properties by detecting at least two pressure measurement values at the at least two pressure sensors within the blood treatment unit with a reference solution,
  b) Optionally comparing the detected pressure measurement values with reference values of the same patient saved on the storage unit which were detected during previous dialysis sessions or with reference values of a patient group saved on the storage unit,
  c) Calculating a substitution target based on the values according to step a) and optionally step b),
  d) Measuring of pressure measurement values at the at least two pressure sensors during a blood treatment,
  e) Comparing the pressure measurement values detected d according to step d) with corresponding reference pressure measurement values saved on the storage unit, and
  f) Adjusting the flow rate of blood, dialysate and/or substituate in case of deviation of at least one measured pressure measurement value from the corresponding reference pressure measurement value saved on the storage unit in order to achieve the substitution target during determined treatment time in an optimal way or to change the treatment time for a given substitution target as less as possible,
wherein the storage unit is configured to identify specific filter properties on the basis of the pressure measurement values measured using the reference solution, and to calculate an optimal substitution target corresponding to the identified filter properties before the beginning of a treatment, and the central processing unit is further so configured that it can detect pressure measurement values during a blood treatment, compare them with corresponding reference pressure measurement values and generate control signals in case of deviations in order to achieve the substitution target in an optimal way.

The storage unit and the central processing unit can be respectively a central processing unit, a hard disk, or an electronic control unit. The storage unit serves particularly and preferably for the identification of specific filter features that are suitable for the determination of the substitution target. For this, information are accessed which are stored, for example in the form of a table or a matrix, and serve preferably by an assignment function, or a control program for the determination of the substitution target. The information on the storage unit serve especially preferably for the identification and assignment of specific filter properties so that the properties of the filter can be detected and the filter type can be identified on the basis of the measured values.

Thereby it is particularly preferred if the filter type is detected within the blood treatment unit in a test run with a reference solution on the basis of the detected pressure measurement values.

For this purpose, respectively at least two simultaneous pressure measurement values which are measured at the at least two of the pressure measuring sensors [PB1], [PB2], [PD1] and [PD2], are used for the calculation of the substitution target.

In further embodiments respectively at least two time-shifted pressure measurement values which are measured by at least one of the pressure measuring sensors [PB1], [PB2], [PD1] and [PD2], are used for the calculation of the substitution target.

Alternatively at least one detected pressure measurement value which is detected by at least one of the pressure measuring sensors [PB1], [PB2], [PD1] and [PD2], can be compared with respective one pressure measurement value corresponding to the pressure measuring sensor saved on the storage unit in order to be used for the calculation of the substitution target.

The information saved on the storage unit can be preferably a matrix, a table, or an assignment function. In a matrix or a table, a specific pressure measurement value is assigned, for example, to a specific flow rate or a specific volume or a specific flow behavior. The assignment function searches corresponding stored values on the basis of the determined values by means of a search algorithm.

The storage unit can further include according to aspects of the invention information relating to additional patient data. These data can relate, for example, to the blood pressure of the patient, the blood flow, the hematocrit of the patient, the total protein concentration of the patient or the patient history, which can be used alone or in combination for determination of the best possible substitution target. Here, the patient history is involved especially for the case that in regard to a substitution target determined as most possible for at least one previous dialysis session complications are occurred in a patient, the best possible substitution target determined for the upcoming dialysis session is reduced below this value recognized as critical value, if it is equal to or greater than this critical value.

In a preferred embodiment, the storage unit is connected to a display, which is used to display the identified information. This embodiment is advantageous because the operating staff can, thus, conveniently, fast and safely retrieve information on the properties and the status of the blood treatment unit or of the blood treatment filter as well as verify easily or follow the effect of control commands. According to aspects of the invention after switching on the blood treatment unit the operating staff runs the reference solution through the system and using the monitor requests the system-relevant information, i.e. particularly information on the filter type, status of the filter and of the system and on the determination of the best possible substitution target. These determinations of the machine status and the best possible substitution target are no treatment methods, as they run or are performed independently of the patient. The configuration of the optimal treatment parameters is done using a reference solution, and not with patient's blood; thus determination of the best possible substitution target is no method for treatment. Thus, also the optional adjustment of the best possible substitution target to changed conditions during the dialysis treatment relates to a method step that is performed without patient material. Thus also the method that provides a variation of the treatment parameters such as the blood flow rate, or dialysate flow rate during the treatment is not a pure treatment method.

The pressure measurement value saved on the storage unit can originate from one or more prior sessions of a specific patient with this specific dialysis machine. It can be used, if necessary, however also measurement values of this patent from other dialysis machine, likewise measurement values from this specific dialysis machine, which are not patient-specific. It can be also, however, standard values known from the literature or device-specific specifications of the manufacturer of the dialysis machine.

With "directly" it is meant that there is no other component between the pressure sensor and the said component. The actual distance between the pressure sensor and said component is herein not decisive, but only that the pressure sensor and the said component are not separated by a further intermediate component. According to aspects of the invention, two pressure sensors are never located directly after one another i.e. without another component between the pressure sensors. Moreover the present invention does not use a pressure sensor in the blood circulation between the patient ☺ and pump P, because such pressure sensors serve for monitoring of the patient and are not suitable for the monitoring of system changes in the tangential flow filter TFF.

In further preferred embodiments, however, a bubble chamber can be arranged between the pressure sensor and the component on blood side, and/or a filter on the dialysate side. But the above-described basic principle is not questioned thereby.

The terms "upstream" and "downstream" are to be understood with reference to the flow direction. If a pressure sensor is "upstream", it is located in flow direction before the component, i.e. the blood or the dialysate passes at first the pressure sensor, and then the component. If a pressure sensor is "downstream", then it is located in flow direction after the component, i.e. the blood or the dialysate passes at first the component and then the pressure sensor. The flow direction can be contrary to each other in the blood circulation and in the dialysis circulation.

The inventive devices for the treatment of blood can comprise further an ultrafiltration pump UFP, a balance chamber system BK and/or a unit for the analysis of the measured pressure measurement values. The ultrafiltration pump is needed for the continuously controlled ultrafiltration and removes from the closed system a precisely set amount of fluid. The same amount that is removed from the closed dialysate circulation is removed in the tangential flow filter TFF from the blood by means of negative pressure. For balancing of the incoming and outgoing flows the balance chamber BK is responsible, thus it is ensured that no fluid is removed from the patient or supplied to the patient unintentionally. The balance chamber can be divided by a flexible separation wall into two chamber halves, which are filled alternately with the ultrafiltrate which is removed from the dialysate circulation, wherein the content of the respective other chamber half is discarded. Optionally, the inventive device further comprises a drip chamber. The drip chamber helps to prevent the intrusion of air into the downstream tubes, by means of a fluid layer acting as an air lock at the bottom of the drip chamber.

The pressure sensors ([PB1], [PB2], [PD1] and [PD2]) are characterized advantageously in that they have a sampling rate of at least 20 Hz. A sampling rate of 20 Hz means that a pressure measurement per pressure sensor is performed 20 times per second.

The terms "on dialysate side" and "on blood side" describe the two circulations which are passed along to one another in the tangential flow filtration, usually by the countercurrent principle, but if necessary, in parallel to the blood stream. Into the hollow fibers of the filter membrane blood/plasma are supplied via a first fluid circulation which flows through them lengthwise. By a second fluid circulation, the dialysate is supplied to the outside of the hollow fibers. Both circulations are separated from each other and are only in contact with each other through the filter membrane.

According to aspects of the invention, a most possible substitution target can be determined in a blood treatment unit thereby that the status of the machine is detected by an operation with a reference solution. The reference solution is used ideally as a standard in the same blood treatment unit or the same blood treatment filter in order to determine the properties of the unit or the system. The reference solution can be exemplarily and preferably a physiological saline; possibly, however, also other salt solutions, glucose solution, purified water, or any other fluid are used, which has the same fluid properties like the reference solution, or from whose behavior the behavior of the reference solution can be concluded.

The reference solution can also be described as test solution with which a test operation of the blood treatment unit can be performed. According to aspects of the invention, thus, during the ultrafiltration of blood for a specific dialyzer an optimal substitution target can be determined that prior to the treatment of a patient a test solution is passed through the dialysis machine.

From the detected pressure measurement values, a substitution target matched to the current state of the dialysis machine can be determined. To this, the inclusion of at least two pressure measurement values is required, which are selected from the above-mentioned pressure measurement values PB1, PB2, PD1 and PD2. According to aspects of the invention, for this respectively absolute pressures, relative pressures, absolute pressure differences between two pressure measuring sensors, relative pressure differences between two pressure measuring points, i.e. between two pressure measuring sensors, absolute pressure amplitudes, relative pressure amplitudes, differences between the absolute pressure amplitudes at two pressure measuring points, i.e. at two pressure measuring sensors or differences between the relative pressure amplitudes at two pressure measuring points, i.e. at two pressure measuring sensors or a combination thereof can be used as measuring signal. This optimal substitution target represents the amount of the substitution solution, which must be supplied to the patient for the maintenance of his blood volume and thus his homeostasis. For determination of the optimal substitution target, the pressure measurement values to be included must be output to a central processing unit. In this central processing unit, the incoming values are processed such that, for example, a good momentum transfer via the membrane is a requirement for a high substitution volume and thus represents a critical factor. A strikingly high value for PB1, for example, caused by a very low flow area, is an indication to select no maximum substitution volumes, since high substituate flows mean in the post-dilution that in the filter an increased hemoconcentration occurs and thus PB1 even further increases. This can cause in the extreme case pressure warnings/alarms.

Such data are recorded during the test measurement and a value for the extend of the characteristic as well as a value for the importance are assigned to them. From the plurality of this information, the substitution target for the treatment is calculated. This calculation can be done for example by a fuzzy logic or in a simple case a substitution target is saved on the storage unit for every possible combination of values.

The so determined optimal substitution target can be displayed via the central processing unit. Thereby the staff in charge can make suitable preparations in order to provide, if necessary, sufficient substitution solution for the expected treatment time of the following dialysis session. The output can be made via a display at the dialysis machine itself or on a peripheral display. In other preferred embodiments, the determined optimal substitution target is automatically forwarded to the dialysis machine, whereby at this the necessary adjustments are made in order to achieve the optimal substitution target. In preferred embodiments, this is only the substitution target. This process can also be performed automatically.

In another preferred embodiment, the measured values can be compared with patient data saved on the storage unit and corresponding measures can be taken. I.e. by comparison with values from particularly good performed treatments the best achievable substitution target can be determined corresponding to the used filter and treated patient or patient group.

In other embodiments the optimal substitution target can be determined in the first minutes of a dialysis session directly from the blood flow of the patient. A run with a test solution is in these embodiments not necessary or provided. The determination of the optimal substitution target and the implementation of the result are performed analogously to the previously described embodiments.

The inventive method for determination of the optimal substitution target is thus substantially simpler than conventional methods, in regard to most of them firstly at least one patient-specific blood parameter such as hematocrit and protein concentration must be determined in the laboratory, or rather vague clues, like the patient history are taken into account. The inventive method is here substantially more purposeful, since the current status of the dialyzer is the critical indicator for the process of the following dialysis session. Hereby measurement values are used, which are recorded anyway for the operation of the dialyzer. This means that no more lead time must be accepted and no additional costs, such as for laboratory analysis are incurred. In addition, the substitution target can be adjusted during the dialysis procedure if changes in the flow behavior indicate that the previously calculated optimal substitution target cannot be achieved. Hereby, it makes use of the same measurement methods as for the determination of the initial configuration. Therefore, adjustments can be performed more purposeful, since the measurement values guarantee comparability.

In further preferred embodiments, however, the pressure measurement values determined in such manner can be combined with previously detected measurement values for blood flow, hematocrit, protein concentration and patient history in the central processing unit.

Another advantage of the use of saline solution as a test solution is that this serves at the same time for cleaning of the dialyzer, because a large portion of the residues from the preceding treatment is washed out. By such a method, two work steps can be carried out in one. For cost reasons, it has—especially in the U.S.—increased lately to clean the dialysis filter, instead of taking a new one per patient and session.

In this case the solution spent for the cleaning can be at the same time also the reference solution for the evaluation of filter properties.

The calculated substitution target can be monitored and adjusted during the treatment in predefined intervals In preferred embodiments, the selected pressure parameters are monitored continuously. Upon exceeding of a predetermined threshold value, thereupon an adjustment of the substitution flow is initiated. Offsetting of the incoming pressure measurement values is performed by the same method as described above. The continuous adjustment of the substitution target can also be performed via the operator and/or an automatic adjustment of substituate flow.

Characteristically, the mechanisms which have an influence on the filter properties, such as the protein concentration polarization, the secondary membrane (the load of the filter membrane with blood cells such as thrombocytes and other blood components), or the clotting, has negative effect on the filtration potential. In these cases, the substitution target must be adjusted downward, i.e. there is a reduction in the substitution flow.

As this can affect the quality of the treatment, it is necessary to consider a further possibility, maintaining or restoring the filter properties during the treatment.

If a too high hematocrit should be determined or suspected as cause for clotting of the dialysis filter, according to aspects of the invention there is the option to perform hemodilution during the dialysis procedure in order to counteract any further deterioration of the dialysis performance. Typically, administration of an anti-coagulant like heparin or heparan sulfate takes place, but any other approved blood-thinning agent or anti-coagulant e.g. marcomar or clopidogrel can also be used. In preferred embodiments, there is on the dialysis machine additionally a reservoir which is filled with a solution of the blood-thinning agent ready for use. In case of indication from this reservoir by means of a perfusor via a valve, the solution with the blood-thinning agent can be fed in defined amounts per time unit or, alternatively as single bolus into the blood circulation. The operation or activation of this valve is performed manually by the dialysis personal or by an automatic monitoring system which is controlled by the central processing unit.

In other preferred embodiments, there is alternatively a port to the blood flow through the dialyzer the blood-thinning agent is, for example, infused through a infusion tube or injected as a single bolus.

In the opposite case that a decreased flow resistance (PBE-PV) on blood side is measured, and this coincides with a low hematocrit of the patient, accordingly, a reduction of the heparin dosage can be proposed or initiated.

If it is determined during continuous or sequential monitoring of the filter properties that the achievement potential has been deteriorated, following countermeasures can be initiated:
i. anticoagulation of the blood by adding an anticoagulant such as heparin
ii. rinsing the dialyzer with a saline or an aqueous solution of sodium chloride and citrate.
iii. dialysate- and/or blood-side pressure pulsation is initiated
iv. blood-thinning before the dialyzer, for example by physiological saline
v. dialyzer replacement It has been found as particularly advantageous to select an ultrafiltration pattern, the pace with which the ultrafiltration rate or the substitution is increased at the beginning of therapy, is kept low. This is as more important, as higher the final value (the substitution target) to be achieved is.

This pace of change or the differential of the ultrafiltration rate of the pressures on dialysate side or their pressure amplitudes absolute or relative to the pressures on blood side can be used as control parameters. If these should be changed too fast or the differential became too large, the slope of the UF-ramp (pace of change of UF rate) will be adjusted. Hereby, it has been shown that lower slope rates are advantageous because such the formation of a secondary membrane has less pronounced effects on the permeability.

With inclusion of the patient history in the determination of the respective substitution target it is meant that information will be made available for the operating person and/or the central processing unit, if the selected ultrafiltration rate should cause complications in the previous dialysis sessions. It should be aspired to stay below this ultrafiltration rate decided as too high. If in the calculation of the optimal substitution target a value results, which is over this critical ultrafiltration rate, it is preferred that the optimal substitution target is adjusted accordingly downwards. In preferred embodiments, by the central processing unit a proposal can be made or displayed, which includes a treatment proposal or a new substitution target, wherein said patient history is considered.

A drop in blood pressure or hypotensive phases is one of the most common complications in dialysis patients. Therefore, the blood pressure of these patients can be monitored during the dialysis. If now a drop in blood pressure or a hypotensive phase is diagnosed, according to aspects of the invention, the ultrafiltration rate, and the flow of the substitution solution can be reduced by dialysis personal or automatically or such a measure can be proposed by the central processing unit. Furthermore, it is possible to change temporarily in the hemofiltration mode or propose such a change. Also a combination of both is possible.

For all signals of the respective pressure measuring sensors or the parameters derived from them, tolerance intervals can be determined in advance, within which the pressure measurement values can fluctuate, without being classified as critical deviation. The measurement tolerance of the sensor depends on various sources, namely on the one hand on the tolerance of the sensor itself, which is generally given by the manufacturer, but also on certain environmental conditions; further on the variability of the medium, i.e. temperature and composition of the flowing fluids; and changes of the system which, for example, can be occurred by contaminations or deposits on the sensors. The tolerance range takes into account a certain measurement uncertainty and empirical experience, to which value deviations from the nominal value have no effect on the function of the system. This means that the deviation or fluctuation of the value or the parameter from the nominal state does not need any regulatory measure. If the detected pressure measurement values or parameters are within the tolerance range, no regulations such as change of the flow rate of blood, dialysate or substituate are necessary. For example, these tolerance intervals can be configured at the central processing unit by input or have been stored on this or be selectable from a given list of a menu command. For the determination of such a tolerance interval, the pressure measurement values detected during a treatment session can be used optionally in combination with the blood flow, the hematocrit of the patient, the total protein concentration of the patient or the patient history, or a combination thereof. Empirically, tolerance intervals are preferred in the range of 0.1% to 100%. More preferred are values between 5% and 70% and most preferred values are between 15% and 50%. However, if one has very low values of the respective treatment parameters, a relative tolerance interval of 100% cannot be expedient, why an additional tolerance interval is defined by absolute values. This represents the minimum value for the tolerance.

The tolerance ranges can preferably refer to values which are measured at the same sensor. The comparison of the detected value is performed with a corresponding tolerance interval which has been saved on the storage unit. If the measured value is within the tolerance range, no regulation is required. If the measured value is not within the tolerance range, a control command for the change e.g. of the blood flow rate is given. For the comparison of the values with the tolerance range, also quotients, differences, sums or products of several values detected at particular different sensors can be used. Particularly preferred is the use of values which were detected at two sensors. Thereby, differences between sensor values are preferably calculated, which are located on the same side of the filter membrane, i.e. both are on blood side or dialysate side. However, it is also preferred if differences are calculated, which are located on two different sides of the filter membrane, i.e. one is on blood side and one is on dialysate side.

In case of a leaving the tolerance range (tolerance interval) of PD1 or PD2 or their pressure amplitudes absolutely or relatively by falling values (in the direction of smaller values), for example, a pulsation can be started or increased on the dialysate or blood side or the current ultrafiltration rate and the substitution flow can be reduced or these measures can be proposed. In case of a leaving the tolerance range tolerance interval of PD1 or PD2 or their pressure amplitudes absolutely or relatively in the direction of increasing values, on the contrary, a pulsation can be stopped or decreased on the dialysate or blood side or the current ultrafiltration rate and the substitution flow can be reduced or these measures can be proposed. Thereby, the central processing unit compares the detected pressure measurement values with corresponding reference pressure measurement values in consideration of a tolerance range, and proposes in case of deviations beyond the tolerance range measures in order to achieve the substitution target during given treatment time in an optimal way or to change for a given substitution target the treatment time as little as possible, usually to extend it as little as possible.

In case of a leaving the tolerance range of the pressures on blood side by a reduced resistance in the blood flow direction, a decrease of the rinsing rate, a lower blood dilution, or a change of the blood flow can be proposed or initiated.

A schematic flow system with the following components is shown in FIG. 1: A pump P, preferably a peristaltic pump, generates the desired flow in the extracorporeal circulation. In the blood circulation shown in dashed lines, the blood from the patient ☺ passes firstly the pump P, and then the first pressure sensor [PB1] on blood side, the tangential flow TFF and before it flows back into the patient ☺, yet another pressure sensor [PB2]. By the countercurrent principle, dialysate is pumped through the filter TFF. In the dialysis circulation shown by solid lines in the flow direction, before the filter TFF the first pressure sensor [PD1] on dialysate side is located and after the filter TFF the second pressure sensor [PD2] is located. The balance chamber BK is provides the balancing of incoming and outgoing flows, thus, it is ensured that no fluid is removed from the patient ☺ or supplied to the patient involuntarily. The weight loss prescribed for the therapy is generated by the ultrafiltration pump UFP which bypasses the balance chamber, BK.

BRIEF DESCRIPTION OF THE DRAWINGS

FIG. 2A and FIG. 2B are pressure curves of the high-flux filters, FIG. 2C and FIG. 2D of the low-flux filters, wherein the filters have the same size.

EXAMPLES

Example 1

Figure 1:
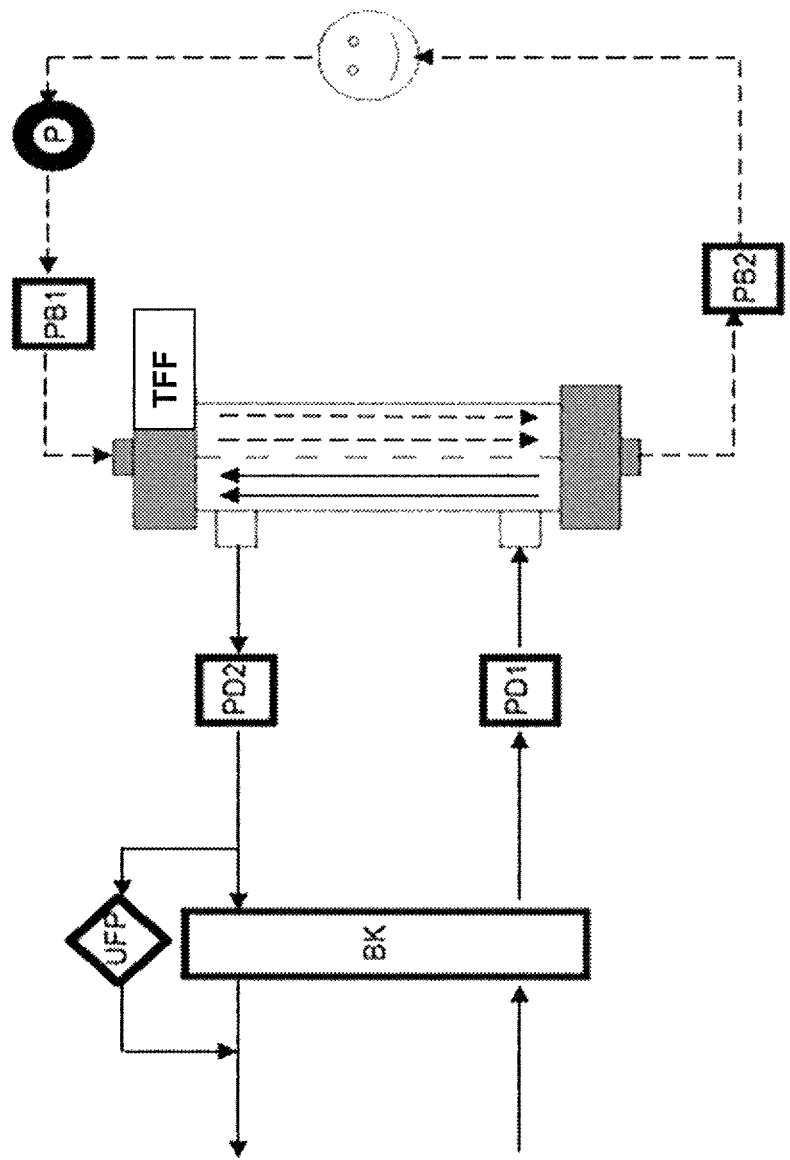
FIG. 1: Scheme for a flow system typically for the invention.
Figure 2A:
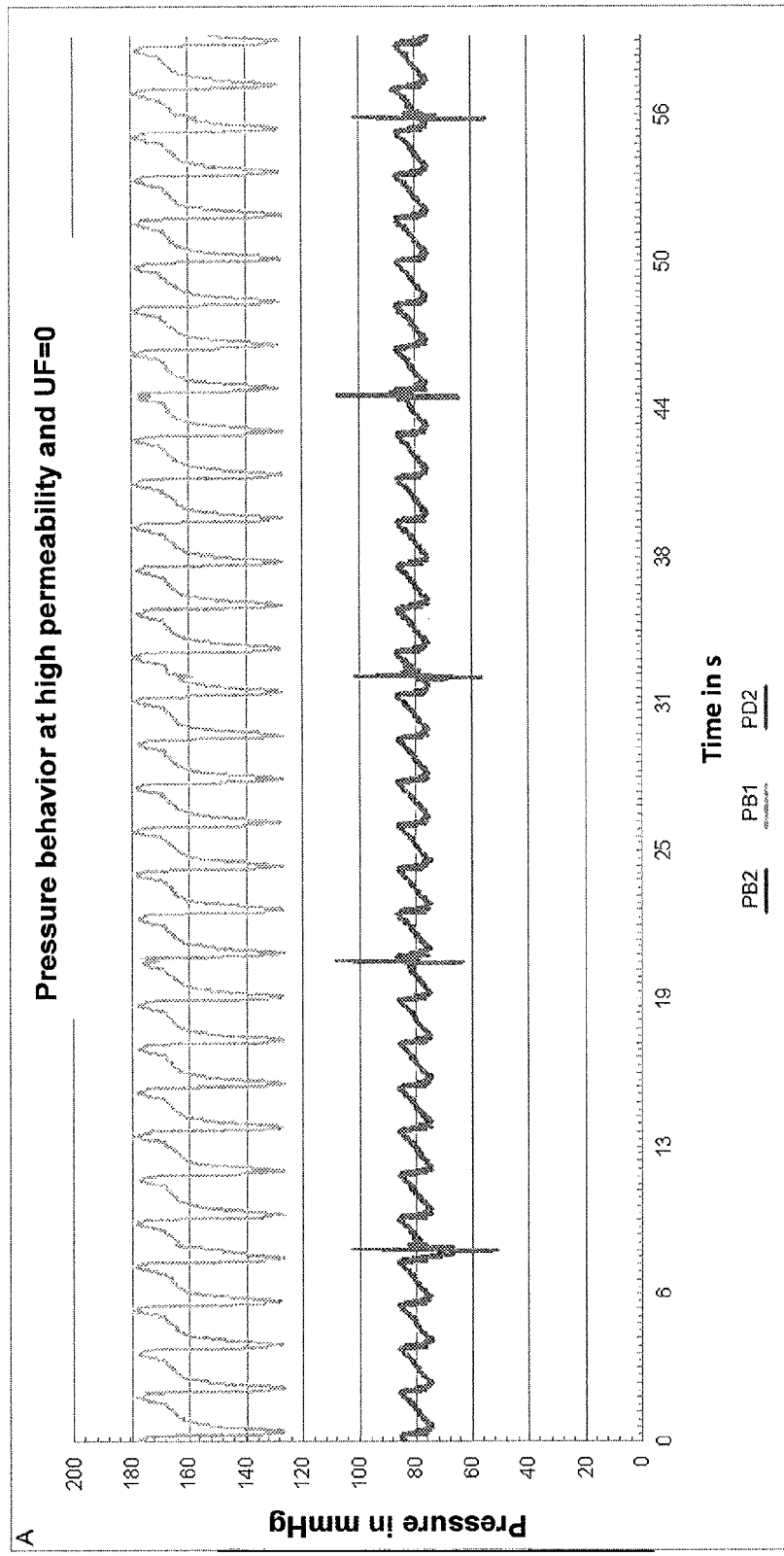
FIGS. 2A, 2B, 2C and 2D: Comparison of various filters.
Figure 2B:
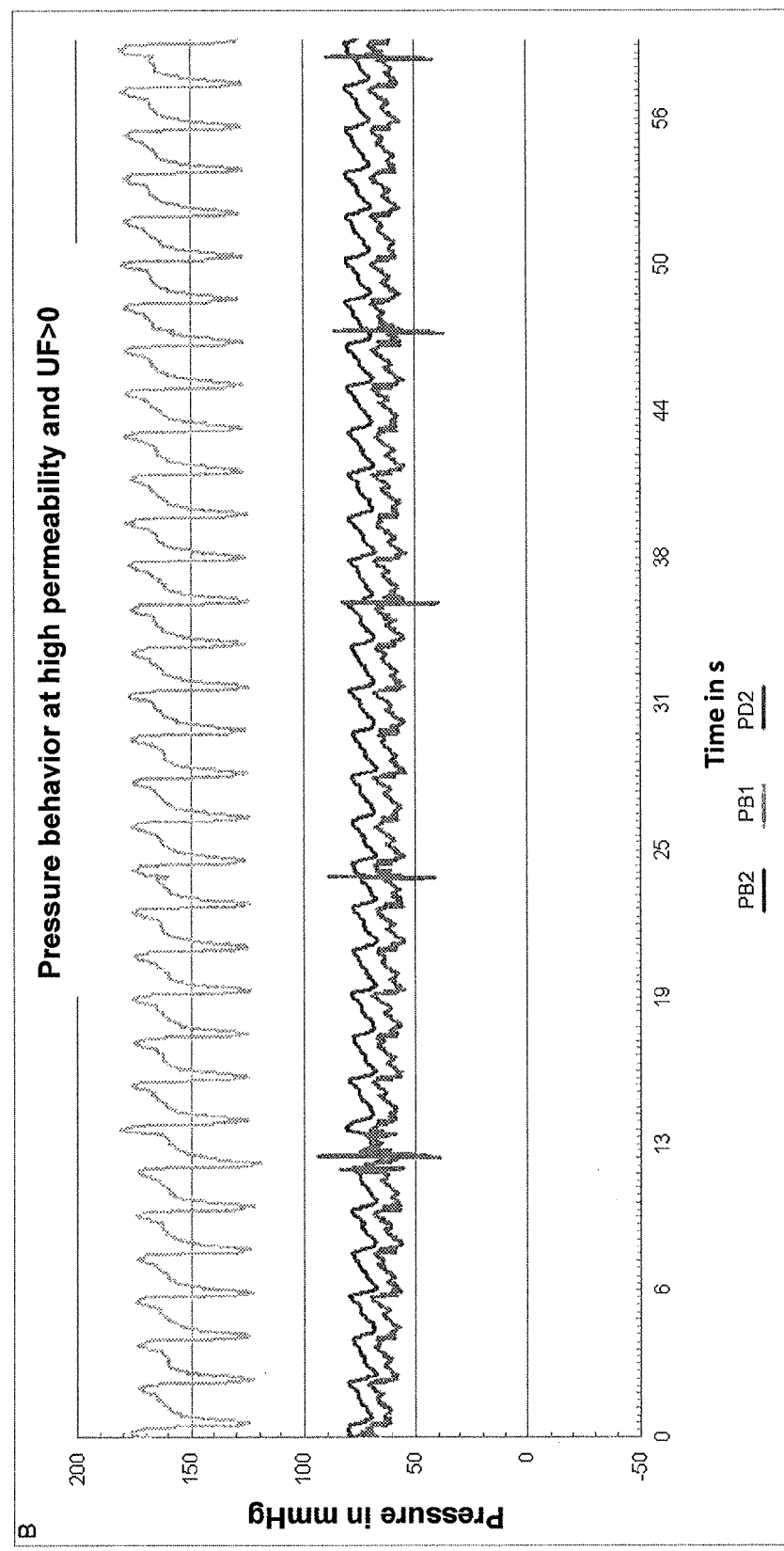
Figure 2C:
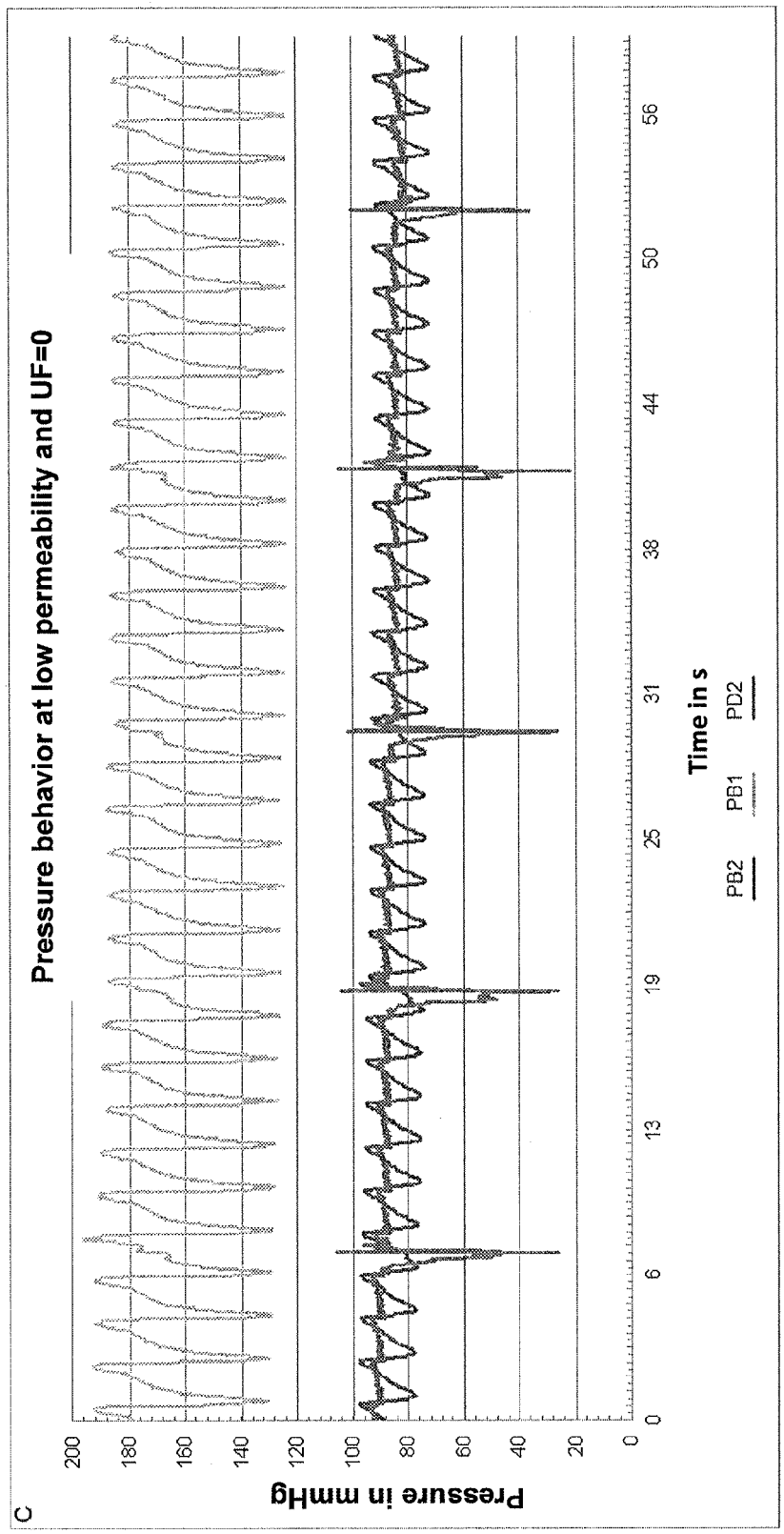
Figure 2D:
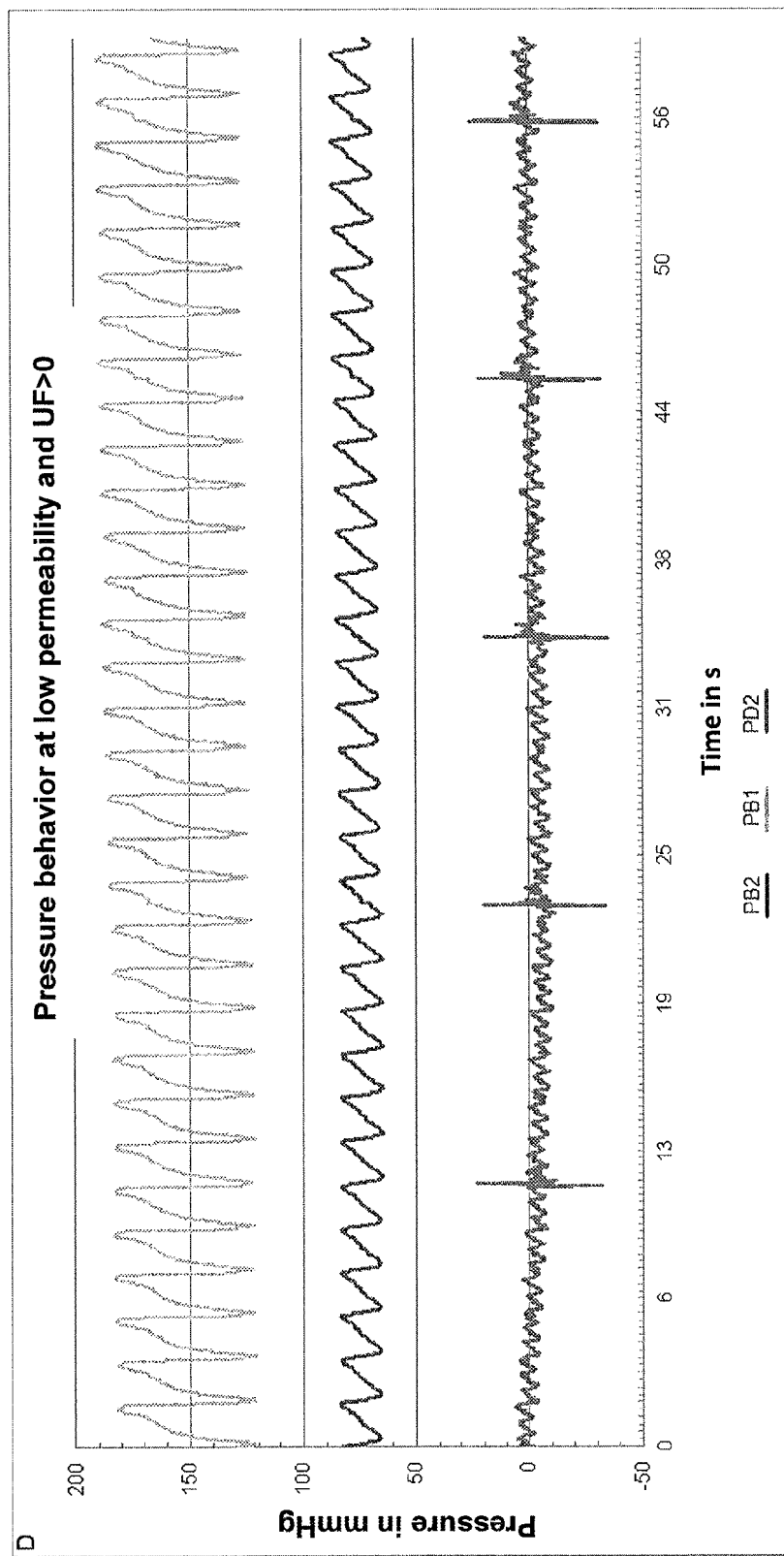
Figure 3:
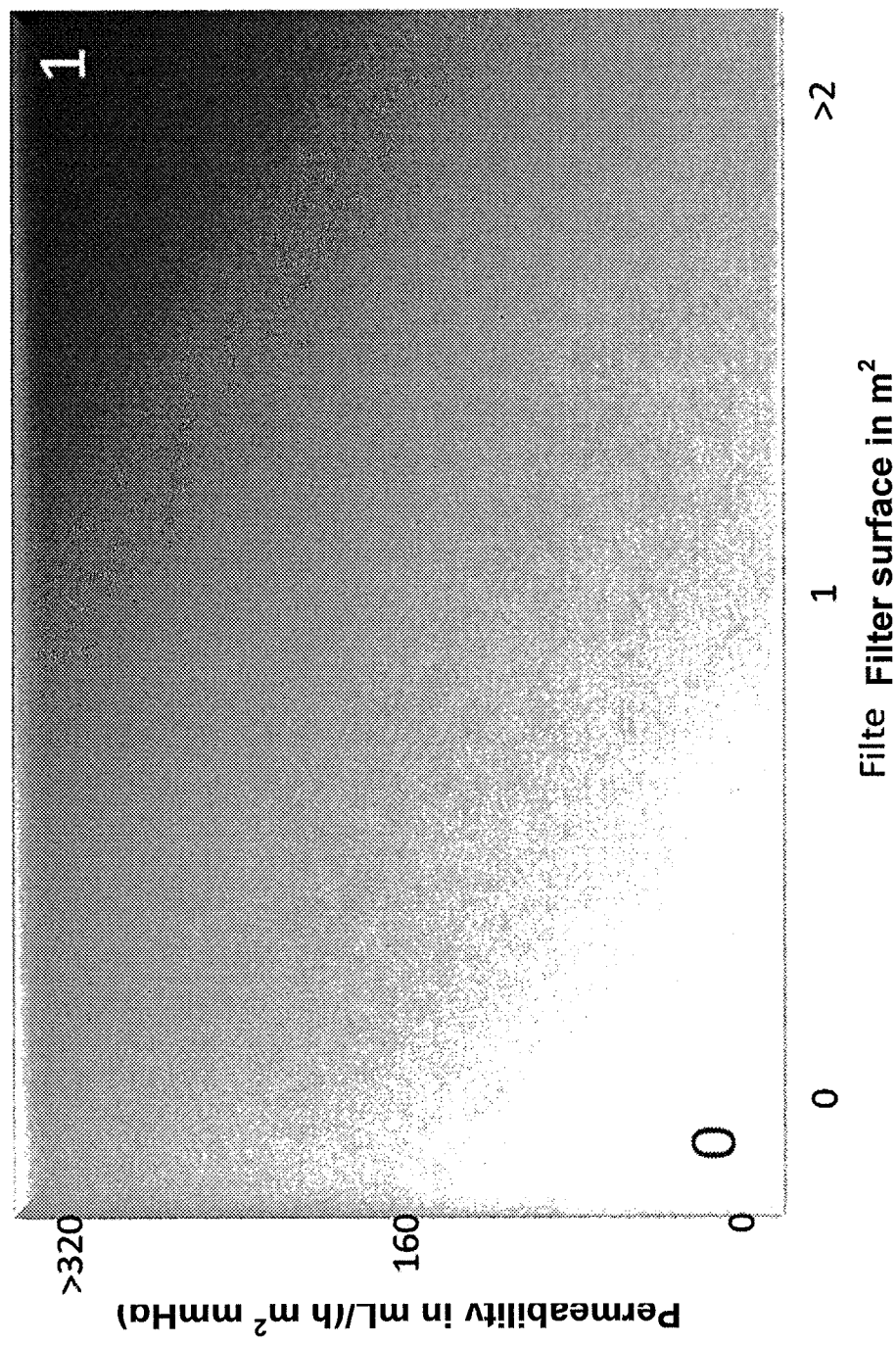
FIG. 3: Matrix for the determination of the factor p.

Therapy Process without Necessity of a Readjustment
a. i) The pressure measurement at two pressure sensors has shown that the filter has a very high permeability value and thus, is suitable for high transmembrane flows. p results in 1.
 ii) Beside the blood flow (300 ml/min), no other variable is known.
 iii) According to the formula $Q_{sub}=[(\frac{1}{3}+BF^*T)-WL]^*p$ (1) a substitution rate of 100 ml/min is determined and thus for a treatment time of 240 min a substitution target of 24 l is calculated.
 iv) Automatic selection of the substitution target by the described procedure to 24 l.
b. Start of the therapy,
c. sequential or continuous monitoring of the pressures and optionally of parameter derived therefrom,
d. after treatment process without disturbance, achievement of the substitution target of 24 l at the end of the dialysis session after 240 minutes.

Example 2

Therapy Process with Readjustment by Sequential Monitoring
a. i) The pressure measurement at two pressure sensors has shown that the filter has a very high permeability value and thus is suitable for high transmembrane flows. p results in 1.
 ii) Beside the blood flow (200 ml/min) no other variable is known.
 iii) According to the formula $Q_{sub}=[(\frac{1}{3}+BF^*T)-WL]^*p$ (1) a substitution rate of 100 ml/min is determined and thus for a treatment time of 240 min a substitution target of 24 l.
 iv) Automatic selection of the substitution target by the described procedure for 24 l.
b. Start of the therapy,
c. sequential monitoring of the parameters shows that the quotient $A_{PD2}/A_{PB1}$ is fallen to less than 70% of the initial value. The previously determined tolerance interval of 30% is thus exceeded.
d. The substituate flow is reduced by 10% and the monitoring is reset.
e. End of therapy: the control parameters have varied due to the readjustment of the flow rates within the desired limits.

Altogether, during the dialysis session of 240 minutes a substitution volume of 22 l was achieved.

Example 3

Therapy Process with Readjustment by Continuous Monitoring a. i) The pressure measurement at two pressure sensors has shown that the filter has a very high permeability value and thus is suitable for high transmembrane flows. p results in 1.
  ii) At a blood flow of 300 ml/min the initial hematocrit is 30% and the maximum hematocrit is 47%.
  iii) According to Qsub=[BF*{1−[Hct(one)/Hct(max)]}−WL]*p at a blood flow rate of 300 ml/min, an initial hematocrit of 30% and a maximum hematocrit of 47%, a substitution target of 27 L is calculated for a four-hour therapy.
b. Start of the therapy,
c. Continuous monitoring of the pressures at a blood-side and a dialysate-side pressure sensor.
d. it is determined that the substitution target will not be achieved at the end of the four-hour blood treatment. PD2 is decreased too strong and has left the predetermined tolerance interval of 35% downward.
e. A reduction of the substituate flow rate by 10% is performed and the pressure profile is again within the tolerance interval.
f. Further continuous monitoring of the pressures
g. End of the therapy: The control parameters have varied due to the readjustment of the flow rates within the desired limits. Altogether, after 4 hours a substitution volume of 24 l was achieved.

Example 4

Therapy Process with Readjustment by Continuous Monitoring a. i) The pressure measurement at three pressure sensors has shown that the filter has a very high permeability value and thus is suitable for high transmembrane flows. p results in 1.
  ii) At a blood flow of 400 ml/min the initial hematocrit is 30% and the maximum hematocrit is 40%.
  iii) According to Qsub=[BF*{1−[Hct(one)/Hct(max)]}−WL]*p at a blood flow rate of 400 ml/min, an initial hematocrit of 30% and a maximum hematocrit of 40%, a substitution target of 26 L is calculated for a four-hour therapy.
b. Automatic selection of the substitution target by described procedure to 26 l.
c. Start of the therapy,
d. Continuous monitoring of the pressures at three pressure sensors,
e. it is determined based on the frequency spectrum of the pressure measurement values at the three pressure sensors that the substitution target will not be achieved at the end of the five-hour blood treatment, because two of the three detected pressure measurement values deviate more than 25% from the stored reference pressure measurement values,
f. a readjustment of the blood flow rate and the substituate flow rate is done,
g. after single readjustment, the measured three pressure measurement values are within the tolerance range of 25% of the reference pressure values,
h. end of the therapy: The dialysis parameters have varied due to the readjustment within the desired limits of the reference pressure measurement values. Altogether, after five-hour blood treatment a substitution volume of 25.5 l was achieved.

Example 5

Determining a Specific Filter Type by the Detection of Pressure Measurement Values by at Least Two Pressure Sensors Using a Reference Solution a. i) Based on the analysis of the pressure amplitudes $A_{PB2}/A_{PD1}$ and $A_{PD2}/A_{PB1}$ the filter is identified by means of comparison with a reference table and a p=1 is assigned.
  ii) Beside the blood flow (300 ml/min) no further variable is known.
  iii) According to the formula $Q_{sub}=[(⅓+BF*T)−WL]*p$ (1), a substitution rate of 100 ml/min is determined and thus for a treatment time of 240 min a substitution target of 24 l is calculated.
  iv) Automatic selection of the substitution target by the described procedure to 24 l.
b. Start of the therapy,
c. sequential or continuous monitoring of the pressures and optionally of parameters derived therefrom,
d. after treatment process without disturbance, achievement of the substitution target of 24 l at the end of the dialysis session after 240 minutes.

Example 6

Identifying a Filter Unsuitable for a HDF Therapy a. i) At start-up of the ultrafiltration of 0 ml/h to 2000 ml/h, the PD2 decreases by more than 50 mmHg.
  ii) This would mean that the filter is unsuitable for a HDF therapy (p<0.5).
b. To the user a warning is issued that a HDF therapy with this filter is not feasible.

The invention claimed is:

1. Method for the attainment of a predetermined substitution target in a blood treatment unit, which comprises the following steps:
  a) Determining the filter properties by detecting at least two pressure measurement values by at least two pressure sensors within the blood treatment unit using a reference solution, prior to connecting a patient with the blood treatment unit,
  b) Comparing the detected pressure measurement values with reference values of the same patient which were detected in previous dialysis sessions or with reference values of a patient group,
  c) Calculating the substitution target based on the values according to at least one of step a) or step b), prior to a current blood treatment of a patient with the blood treatment unit,
  d) Measuring of pressure measurement values by at least two pressure sensors during the current blood treatment,
  e) Comparing the pressure measurement values measured according to step d) with reference pressure measurement values,
  f) Configuring a blood flow rate, a dialysate flow rate, or a substituate flow rate in case of deviation of at least one detected pressure measurement value from the reference pressure measurement value in order to achieve the substitution target for a given treatment time or to modify the treatment time for a given substitution target as little as possible.

2. Method according to claim 1, wherein the reference pressure measurement values were recorded according to step e) during blood treatments, in which the substitution target has been achieved during the treatment time.

3. The method according to claim 1, wherein the reference solution is selected from a group consisting of a physiological saline solution, a physiological salt solution, a glucose solution, and purified water.

4. A blood treatment unit with a dialyzer, comprising:
at least two pressure sensors configured to detect at least two pressure measurement values within the blood treatment unit;
a storage unit; and
a central processing unit adapted to:
determine filter properties with the detected at least two pressure measurement values prior to connecting a patient with the blood treatment unit, using a reference solution;
compare the detected at least two pressure measurement values with a set of reference values stored on the storage unit, the set of reference values being at least one of:
detected in a previous treatment of the patient; or
from a patient group;
calculate a substitution target based on the determined filter properties and the compared pressure measurement values and set of reference values prior to the current treatment; and
configure at least one of a blood flow rate, a dialysate flow rate, or a substituate flow rate of the blood treatment unit to achieve the substitution target for the current treatment when at least one detected pressure measurement value deviates from the set of reference values.

5. The blood treatment unit of claim 4, wherein the reference solution is selected from a group consisting of a physiological saline solution, a physiological salt solution, a glucose solution, and purified water.

6. The blood treatment unit according to claim 4, wherein the at least two pressure sensors are further configured to measure pressure measurement values during the current treatment of the patient with the blood treatment unit, and
the central processing unit is further adapted to:
compare the pressure measurement values measured during the current treatment to the set of reference values saved on the storage unit, and reconfigure the blood treatment unit by controlling at least one of a blood flow rate, a dialysate flow rate, or a substituate flow rate in case of a deviation of at least one pressure measurement value during the current treatment from the set of reference values in order to achieve the substitution target for a given treatment time or to modify the treatment time for a given substitution target as little as possible.

7. The blood treatment unit according to claim 6, wherein the central processing unit is further configured to control at least one of a blood flow rate, dialysate flow rate, or a substituate flow rate based on a mathematical relation between the detected pressure measurement values and the blood flow rate.

8. Blood treatment unit according to claim 6, wherein the central processing unit is further configured to control at least one of a blood flow rate, a dialysate flow rate, or a substituate flow rate to achieve the substitution target based on a mathematical relation between the detected pressure measurement values and a hematocrit of the blood.

9. The blood treatment unit according to claim 6, wherein the central processing unit is further configured to control at least one of a blood flow rate, a dialysate flow rate, or a substituate flow rate based on a mathematical relation between the detected pressure measurement values and a proportion of a non-membrane-permeable blood components.

10. The blood treatment unit according to claim 6, wherein the set of reference values are recorded during one or more blood treatments, in which the substitution target is achieved during a treatment time.

11. The blood treatment unit according to claim 4, wherein the central processing unit is further configured to determine the filter properties by determining a filter type from reference values of the filter type saved in the storage unit.

12. The blood treatment unit according to claim 4, wherein the substitution target is determined by analysis of pressure measurement values detected at three pressure sensors.

13. The blood treatment unit according to claim 4, wherein the substitution target is determined by analysis of pressure measurement values detected at four pressure sensors.

14. The blood treatment unit according to claim 4, wherein the central processing unit is further configured to compare the detected at least two pressure measurement values with the set of reference values in consideration of a tolerance range, and in case of deviations from the tolerance range is configured to propose actions in order to achieve the substitution target for a given treatment time in an optimal way or to modify the treatment time for the substitution target as little as possible.

15. The blood treatment unit according to claim 4, wherein the central processing unit is further adapted to configure at least one of a blood flow rate, a dialysate flow rate or a substituate flow rate to achieve the substitution target automatically.

16. The blood treatment unit according to claim 4, wherein the central processing unit is further configured tocontrol at least one of a blood flow rate, dialysate flow rate or a substituate flow rate to achieve the substitution target based on a mathematical relation between the detected pressure measurement values and the blood flow rate.

17. The blood treatment unit according to claim 4, wherein the central processing unit is further configured to control at least one of a blood flow rate, a dialysate flow rate or a substituate flow rate to achieve the substitution target based on a mathematical relation between the detected pressure measurement values and a hematocrit of the blood.

18. The blood treatment unit according to claim 4, wherein the central processing unit is further configured to control at least one of a blood flow rate, a dialysate flow rate, ora substituate flow rate to achieve the substitution target based on a mathematical relation between the detected pressure measurement values and a proportion of at least one non-membrane-permeable blood component.

* * * * *